US006177528B1

(12) United States Patent
LaPointe et al.

(10) Patent No.: US 6,177,528 B1
(45) Date of Patent: Jan. 23, 2001

(54) SUBSTITUTED AMINOMETHYLPHOSPHINES, COMPOSITIONS AND COORDINATION COMPLEXES OF SAME, THEIR SYNTHESIS AND PROCESSES USING SAME

(75) Inventors: Anne Marie LaPointe, Santa Clara; Anil Guram, Cupertino; Timothy S. Powers, San Francisco; Bernd Jandeleit, Palo Alto; Thomas Boussie, Menlo Park; Cheryl Lund, Milpitas, all of CA (US)

(73) Assignee: Symyx Technologies, Inc., Santa Clara, CA (US)

( * ) Notice: Under 35 U.S.C. 154(b), the term of this patent shall be extended for 0 days.

(21) Appl. No.: 09/460,071

(22) Filed: Dec. 14, 1999

Related U.S. Application Data

(60) Division of application No. 09/264,306, filed on Mar. 8, 1999, now Pat. No. 6,043,363, which is a continuation-in-part of application No. 09/037,162, filed on Mar. 9, 1998, now Pat. No. 6,034,240.

(51) Int. Cl.$^7$ .................. C08F 4/44; C08F 4/06; C08F 110/02; C07F 19/00; C07F 9/02

(52) U.S. Cl. ............... 526/139; 526/141; 526/161; 526/172; 526/317.1; 526/351; 526/352; 526/943; 502/102; 544/225; 544/337; 546/2; 546/10; 546/22; 556/21; 556/28

(58) Field of Search ............... 556/21, 28; 544/225, 544/337; 546/2, 10, 22; 564/15; 502/102; 526/139, 141, 161, 172, 317.1, 351, 352, 943

(56) References Cited

U.S. PATENT DOCUMENTS

| 3,553,265 | 1/1971 | Maier | 260/570.5 |
|---|---|---|---|
| 5,576,460 | 11/1996 | Buchwald | 564/386 |

OTHER PUBLICATIONS

Abd–Ellah et al., "Synthesis and Reactivity of Some Organophosphorus Derivatives of Schiff Bases", *Gazzetta Chimica Italiana*, 118, pp. 141–143 (1988).

Abd–Ellah et al., "Synthesis and Characterization of Some New Complexes of Phosphine Schiff Base Derivatives," *Proc. Indian Natn. Sci. Acad.*, vol. 55, No. 4, pp. 678–682 (1989).

Arbuzov et al., "Reaction of Dihydroxymethyl Phenylphosphine with Isobutyl Ester of Diphenylboric Acid in the Presence of Ritriles,"*Izv. Akad. Nak. SSSR, Ser, Khi*, vol. 3, pp. 676–679 (1982).

Heinicke, et al., "Synthesis of 1,3–Azaphopholines–1" *Z. Chem*, vol. 26, No. 1, pp. 407–408 (1986).

Arbuzov et al., "Synthesis and Structure of 1,5–Diaza–3, 7–Diphosphacyclooctanes" *Izv. Akad. Nak. SSSR, Ser. Khi*, vol. 8, pp. 1846–1850 (1983).

Anders et al., "Remote Controlled Nucleophilicity, 2$^1$: Lithiated Cα–Substituted 4–Methylpyridines" Synthesis 12: 1221–1227 (1991).

Kellner et al., "Dia–Mannich–Reaktion als Synthesekonzept in der Phosphinchemie", Z. Chem. 24: 365–374 (1984).

Grim et al., "The Synthesis and Characterization of some novel polydentate phosphouros–nitrogen ligands" Tetrahederon Ltrs 31: 2951–2953 (1973).

Reetz et al., "β–Cyclodextrin–Modified Diphosphanes as Ligands for Supramolecular Rhodium Catalysts" Agnew. Chem. Int. Ed. Engl. 36 (8): 865–867, (1997).

McLain, S., Organmetallic Crown Ethers.. 1. Metal Acyl Binding to a Crown Ether Held Cation: J.Am. Chem. Soc. 105: 6355–6357 (1983).

Shirakawa E., (1997) Tetrahederon Letters 38 (21): 3759–3762 "An iminophosphine–palladium catalyst for cross–coupling of aryl halides with organostannanes".

Kamikwa, K., (1998) J. Org. Chem. 63 (23): 8407–8409 Palladium–catalyzed amination of aryl bromides utilizing arene–chromium complexes as ligands.

Lapointe, A M, (1999) J. Comb. Chem. 1 (1): 101–104 "Parallel Synthesis of Aminomethylphosphine Ligands".

*Primary Examiner*—Porfirio Nazario-Gonzalez

(57) ABSTRACT

Novel aminomethylphosphine ligands have particular substituents on the central carbon atom. Such ligands form coordination complexes that may be catalysts for the polymerization of monomers or other catalytic induced reactions.

14 Claims, No Drawings

SUBSTITUTED AMINOMETHYLPHOSPHINES, COMPOSITIONS AND COORDINATION COMPLEXES OF SAME, THEIR SYNTHESIS AND PROCESSES USING SAME

This application is a divisional of U.S. patent application 09/264,306, filed Mar. 8, 1999, now U.S. Pat. No. 6,043,363, which is a continuation in part of U.S. patent application 09/037,162, filed Mar.9, 1998, which is incorporated herein by reference.

FIELD OF THE INVENTION

The present invention generally relates to the field of catalysis. In particular, this invention relates to new compounds that are useful as ligands for organometallic complexes that are catalysts for a variety of different reactions. The invention also relates to combinatorial chemistry in that combinatorial techniques were used in connection with this invention.

BACKGROUND OF THE INVENTION

Ancillary ligand stabilized metal complexes (e.g., organometallic complexes) are useful as catalysts, additives, stoichiometric reagents, monomers, solid state precursors, therapeutic reagents and drugs. The ancillary ligand system comprises organic substituents that bind to the metal center (s), remain associated with the metal center(s), and therefore provide an opportunity to modify the shape, electronic and chemical properties of the active metal center(s) of the organometallic complex.

Certain organometallic complexes are catalysts for reactions such as oxidation, reduction, hydrogenation, hydrosilylation, hydrocyanation, hydroformylation, polymerization, carbonylation, isomerization, metathesis, carbon-hydrogen activation, cross-coupling, Friedel-Craftis acylation and alkylation, hydration, dimerization, trimerization, oligomerization, Diels-Alder reactions and other transformations. Organometallic complexes can be prepared by combining an ancillary ligand precursor with a suitable metal precursor in a suitable solvent at a suitable temperature.

One example of the use of organometallic complexes this is in the field of single- sited olefin polymerization catalysis. The active site typically comprises an ancillary ligand-stabilized, coordinatively unsaturated transition metal alkyl complex. Although a variety of such organometallic catalysts have been discovered over the past 15 years, the discovery process is laborious, entailing the individual synthesis of potentially catalytic materials and subsequently screening them for catalytic activity.

It is always a desire to discover new ligand systems that, once connected to a metal center, will catalyze reactions differently from known ligand systems. This invention provides new ancillary ligands that may be attached to a metal center. Once attached, such ligands modify the electronic and steric environment and may catalyze reactions differently from known systems.

SUMMARY OF THE INVENTION

The invention disclosed herein is a new ligand, which can be characterized by the general formula:

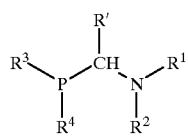

wherein each of $R^1$, $R^2$, $R^3$, and $R^4$ is, independently, selected from the group consisting of hydrogen, allyl, substituted all, aryl, substituted aryl, arylalkyl, substituted arylalkyl, acyl, amino, alkylamino, acylamino, silyl, germyl, stanyl, siloxy, phosphino, aryloxy, aryloxyalkyl, substituted aryloxyalkyl, heteroaryl, substituted heteroaryl, heteroarylalkyl, substituted heteroarylalkyl, heterocycles, substituted heterocycles, heterocyclicalkyl, substituted heterocyclicalkyl S-aryl and S-alkyl mercaptans and combinations thereof. Optionally, $R^1$ and $R^2$ are combined together to form a ring structure. Also optionally, $R^3$ and $R^4$ are combined together in a ring structure. R' is selected from a similar group, with particular exceptions, such as hydrogen.

The ligands of this invention are made in a novel method. The new method is particularly suitable for simultaneous or parallel synthesis of the ligands of this invention, however, serial synthesis is also possible. Generally, the aminomethylphosphines of this invention are prepared by a condensation reaction that combines an amine, a phosphine and an aldehyde, with a variety of substitutions on each, in tetrahydrofuran (THF) at about room temperature.

After synthesis, the ligand is combined with a metal precursor compound to form a composition of matter or a coordination complex in a ligand exchange reaction. The resulting composition or coordination complex is generally useful as a catalyst. For example, the coordination complex may be a single-site catalyst for the polymerization of olefins, diolefms or acetylenically unsaturated monomers, either alone or in combination. Depending on the compound or composition, the catalyst may be activated for polymerization activity through the use of an activator or activating technique. The composition or complex is also catalyst for various cross coupling reactions or other chemical transformations.

Thus, in one aspect of the invention, new ligands are provided that may be combined into a composition or coordination complex usefull as a catalyst.

In another aspect of this invention a new method of synthesis is provided that allows for easy synthesis of the new ligands, where the new procedure does not require refluxing or harsh solvents.

In a further aspect of this invention, new coordination complexes are provided that catalyze chemical reactions, including polymerization or cross coupling reactions.

In yet a flier aspect of this invention, a polymerization process is described employing the coordination complexes of this invention as a or the only component of a catalyst system.

In still a further aspect of this invention, new polymers may be created through the use of a novel polymerization catalyst.

Further aspects of this invention will be evident to those of skill in the art upon review of this specification.

DETAILED DESCRIPTION OF THE INVENTION

The invention disclosed herein is a new ligand combined with metals to form coordination complexes that are useful as catalysts for chemical reactions, particularly polymerization and cross coupling reactions.

As used herein, the phrase "characterized by the formula" is not intended to be limiting and is used in the same way that "comprising" is commonly used. The term "independently selected" is used herein to indicate that the R groups, e.g., $R^1$, $R^2$, $R^3$, and $R^4$, can be identical or different (e.g. $R^1$, $R^2$, $R^3$, and $R^4$ may all be substituted alkyls or $R^1$ and $R^2$ may be a substituted alkyl and $R^3$ may be an aryl, etc.). Adjacent R-groups may be coupled to form cyclic structures. A named R group will generally have the structure that is recognized in the art as corresponding to R groups having that name. For the purposes of illustration, representative R groups as enumerated above are defined herein. These definitions are intended to supplement and illustrate, not preclude, the definitions known to those of skill in the art.

The term "alkyl" is used herein to refer to a branched or unbranched, saturated or unsaturated, monovalent hydrocarbon radical. When the alkyl group has from 1–6 carbon atoms, it is referred to as a "lower alkyl." Suitable allyl radicals include, for example, methyl, ethyl, n-propyl, i-propyl, 2-propenyl (or allyl), n-butyl, t-butyl, i-butyl (or 2-methylpropyl), etc. As used herein, the term encompasses "substituted alkyls." In particular embodiments, allyls have between 1 and 200 carbon atoms, between 1 and 50 carbon atoms or between 1 and 20 carbon atoms.

"Substituted alkyl" refers to alkyl as just described including one or more functional groups such as lower alkyl, aryl, acyl, halogen (i.e., alkylhalos, e.g., $CF_3$), hydroxy, amino, cyano, phosphido, alkoxy, alkylamino, acylamino, acyloxy, aryloxy, aryloxyalkyl, mercapto, both saturated and unsaturated cyclic hydrocarbons, heterocycles and the like. These groups may be attached to any carbon of the alkyl moiety.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include substituted or unsubstituted phenyl, naphthyl, biphenyl, diphenylmethyl and benzophenone among others. In particular embodiments, aryls have between 1 and 200 carbon atoms, between 1 and 50 carbon atoms or between 1 and 20 carbon atoms. "Substituted aryl" refers to aryl as just described including one or more functional groups such as lower alkyl, acyl, halogen, alkylhalos (e.g., $CF_3$), hydroxy, amino, cyano, phosphido, alkoxy, alkylamino, acylamino, acyloxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone.

The term "acyl" is used to describe a ketone substituent, —C(O)X, where X is alkyl or substituted alkyl, aryl or substituted aryl as defined herein.

The term "amino" is used herein to refer to the group —NXX', where X and X' may independently be hydrogen, lower allyl, substituted lower alkyl, aryl, substituted aryl or acyl. When an amino group is bonded to a metal through the nitrogen atom, it is referred to as an "amido" ligand.

The term "alkoxy" is used herein to refer to the —OX group, where X is an alkyl, substituted lower alkyl, aryl, substituted aryl, wherein the substituted alkyl, aryl, and substituted aryl groups are as described herein. Suitable alkoxy radicals include, for example, methoxy, ethoxy, phenoxy, substituted phenoxy, benzyloxy, phenethyloxy, t-butoxy, etc.

As used herein, the term "phosphino" refers to the group —PXX', where X and X' may independently be hydrogen, lower alkyl, substituted lower alkyl, aryl, substituted aryl or acyl.

As used herein, the term "mercapto" defines moieties of the general structure X—S—$X^1$ wherein X and $X^{1a}$re the same or different and are alkyl, aryl or heterocyclic as described herein.

The term "saturated cyclic hydrocarbon" denotes groups such as cyclopropyl, cyclobutyl, cyclopentyl, cyclohexyl, etc. and substituted analogues of these structures.

The term "unsaturated cyclic hydrocarbon" is used to describe a monovalent non-aromatic group with at least one double bond, such as cyclopentene, cyclohexene, etc. and substituted analogues thereof.

The term "cyclopentadienyl" is used to describe an aromatic five carbon ring group, which may be attached via a carbon in the ring, $\eta^5$ bond or any other type of bond that a cyclopentadienyl group is known to form.

The term "substituted cyclopentadienyl" is used to describe a cyclopentadienyl, as just described, that is substituted with one or more functional groups such as lower alkyl, acyl, halogen, alkylhalos (e.g., $CF_3$), hydroxy, amino, phosphido, alkoxy, alkylamino, acylamino, acyloxy, mercapto, etc. "Substituted cyclopentadienyl" is also used to cover situations where the substituent is bis-cyclopentadienyl group, such as ferrocene, tetramethylcyclopentadienyl-dimethylsilyl-pentamethylcyclopentadienyl, bis(tetramethylcyclopentadienyl)dimethylsilyl or other bis-cyclopentadienyl groups.

The term "heteroaryl" as used herein refers to aromatic rings in which one or more carbon atoms of the aromatic ring(s) are substituted by a heteroatom such as nitrogen, oxygen or sulfur. Heteroaryl refers to structures that may be a single aromatic ring, multiple aromatic ring(s), or one or more aromatic rings coupled to one or more nonaromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Heteroarylalkyl" defines a subset of "alkyl" wherein the heteroaryl group is attached through an alkyl group as defined herein.

"Substituted heteroaryl" refers to heteroaryl as just described wherein the heteroaryl nucleus is substituted with one or more functional groups such as lower alkyl, acyl, halogen, alkylhalos (e.g., $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, flran, etc. or benzo-fused analogues of these rings are defined by the term "substituted heteroaryl."

"Substituted heteroarylalkyl" refers to a subset of "substituted alkyls" as described above in which an alkyl group, as defined herein, links the heteroaryl group to the nucleus.

The term "heterocyclic" is used herein to describe a monovalent saturated or unsaturated nonaromatic group having a single ring or multiple condensed rings from 1–12 carbon atoms and from 1–4 heteroatoms selected from nitrogen, phosphorous sulfur or oxygen within the ring. Such heterocycles are, for example, tetrahydrofuran, morpholine, piperidine, pyrrolidine, etc.

The term "substituted heterocyclic" as used herein describes a subset of "heterocyclics" wherein the heterocycle nucleus is substituted with one or more functional groups such as alkyl, acyl, halogen, alkylhalos (e.g., $CF_3$), hydroxy, amino, alkoxy, alkylamino, acylamino, acyloxy, mercapto, etc.

The term "heterocyclicalkyl" defines a subset of "allyls" wherein an allyl group, as defined herein, links the heterocyclic group to the nucleus.

The term "substituted heterocyclicaLkyl" defines a subset of "heterocyclic alkyl" wherein the heterocyclic nucleus is substituted with one or more functional groups such as lower alkyl, acyl, halogen, alkylhalos (e.g., $CF_3$), hydroxy, amino, alkoxy, alkylamino, acylamino, acyloxy, mercapto, etc.

The ligands of this invention can be characterized by the formula:

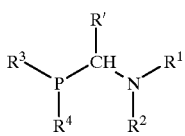

wherein each of $R^1$, $R^2$, $R^3$, and $R^4$ is, independently, selected from the group consisting of hydrogen, alkyl, substituted alkyl, aryl, substituted aryl, arylalkyl, substituted arylalkyl, acyl, amino, alkylamino, acylamino, silyl, germyl, stanyl, siloxy, phosphino, aryloxy, aryloxyalkyl, substituted aryloxyalkyl, heteroaryl, substituted heteroaryl, heteroarylalkyl, substituted heteroarylalkyl, heterocycles, substituted heterocycles, heterocyclicalkyl, substituted heterocyclicalkyl S-aryl and S-alkyl mercaptans and combinations thereof. Optionally, $R^1$ and $R^2$ are combined together to form a ring structure. Also optionally, $R^3$ and $R^4$ are combined together in a ring structure.

R' is selected from the group consisting of alkyl, substituted alkyl, aryl, substituted aryl, arylalkyl, substituted arylalkyl, silyl, germyl, stanyl, phosphino, aryloxy, aryloxyalkyl, substituted aryloxyallyl, heteroaryl, substituted heteroarylalkyl, heteroarylalkyl, substituted heteroarylalkyl, heterocycles, substituted heterocycles, heterocyclicalkyl, substituted heterocyclicalkyl S-aryl and S-alkyl mercaptans and combinations thereof The substituents present on the basic ligand structure play an important role in determining the coordination geometry of the ligand to the metal center. While not wanting to be bound by any particular theory, such geometry differences may also affect the catalytic performance of the resulting coordination complex.

In more particular embodiiments, $R^1$ and $R^2$ are, independently selected from the group consisting of alkyl, substituted alkyl, aryl, substituted aryl, cyclopentadienyl, substituted cyclopentadienyl, heteroaryl, substituted heteroaryl, heteroarylalkyl, substituted heteroarylalkyl, amino, alkoxy, saturated cyclic hydrocarbon, unsaturated cyclic hydrocarbon, heterocyclic, substituted heterocyclic, heterocyclicalkyl, substituted heterocyclicalkyl and combinations thereof More preferably, $R^1$ and $R^2$ are, independently selected from the group consisting of alkyl, lower alkyl substituted aikyl, acyl substituted alkyl, halogen substituted alkyl, alkylhalo substituted alkyl, hydroxyl substituted alkyl, phosphino substituted alkyl, alkoxy substituted alkyl, alkylamino substituted alkyl, acylamino substituted alkyl, acyloxy substituted alkyl, mercapto substituted alkyl, lower alkyl substituted aryl, acyl substituted aryl, halogen substituted aryl, alkyihalo substituted aryl, hydroxyl substituted aryl, phosphino substituted aryl, alkoxy substituted aryl, alkylamino substituted aryl, acylamino substituted aryl, acyloxy substituted aryl, mercapto substituted aryl, cyclopentadienyl, substituted cyclopentadienyl, heteroaryl, substituted heteroaryl, heteroarylalkyl, substituted heteroarylalkyl, amino, alkoxy, saturated cyclic hydrocarbon, unsaturated cyclic hydrocarbon, heterocyclic, substituted heterocyclic, heterocyclicalkyl, substituted heterocyclicalkyl and combinations thereof. Specific examples from which either of $R^1$ and $R^2$ may be chosen are hydride, methyl, ethyl, propyl, isopropyl, benzyl, butyl, s-butyl, t-butyl, 2,4,6-trimethylphenyl, N,3,3'-trimethylaminopropyl, N,2,2'-trimethylaminoethyl, 3-cyano(N-methyl)ethyl, and 2-(2-pyridine)(N-methyl)ethyl.

In other embodiments, $R^1$ and $R^2$ are joined together to form a ring structure having up to 20 non-hydrogen atoms as the combined substituent. More particularly, when $R^1$ and $R^2$ are joined together, they are together selected from the group consisting of heterocyclic, substituted heterocyclic and substituted heterocyclicalkyl. Specific examples from which $NR^1R^2$ may together be chosen are morpholine, N-arylpiperazine (such as N-phenylpiperazine), N-alkylpiperazine (such as N-methylpiperazine and N-ethylpiperazine), and piperidine.

More particular embodiments $R^3$ and $R^4$ are where $R^3$ and $R^4$ are, independently selected from the group consisting of alkyl, substituted alkyl, aryl, substituted aryl, cyclopentadienyl, substituted cyclopentadienyl, heteroaryl, substituted heteroaryl, heteroarylalkyl, substituted heteroarylalkyl, amino, alkoxy, saturated cyclic hydrocarbon, unsaturated cyclic hydrocarbon, heterocyclic, substituted heterocyclic, heterocyclicalkyl, substituted heterocyclicalkyl and combinations thereof. More preferably, $R^3$ and $R^4$ are, independently selected from the group consisting of alkyl, lower alkyl substituted alkyl, acyl substituted alkyl, halogen substituted alkyl, alkylhalo substituted alkyl, hydroxyl substituted alkyl, phosphino substituted alkyl, alkoxy substituted alkyl, alkylamino substituted alkyl, acylamino substituted alkyl, acyloxy substituted alkyl, mercapto substituted alkyl, lower alkyl substituted aryl, acyl substituted aryl, halogen substituted aryl, alkylhalo substituted aryl, hydroxyl substituted aryl, phosphino substituted aryl, alkoxy substituted aryl, alkylamino substituted aryl, acylamino substituted aryl, acyloxy substituted aryl, mercapto substituted aryl, cyclopentadienyl, substituted cyclopentadienyl, heteroaryl, substituted heteroaryl, heteroarylalkyl, substituted heteroarylalkyl, amino, alkoxy, saturated cyclic hydrocarbon, unsaturated cyclic hydrocarbon, heterocyclic, substituted heterocyclic, heterocyclicalkyl, substituted heterocyclicalkyl and combinations thereof. Specific examples from which either of $R^3$ and $R^4$ may be chosen are hydride,.methyl, ethyl, propyl, isopropyl, benzyl, butyl, s-butyl, t-butyl, phenyl, cyclohexyl, 2,4,6-trimethylphenyl, methoxy, ethoxy, n-propoxy, i-propoxy, n-butoxy, s-butoxy, t-butoxy and phenoxy.

In other embodiments, $R^3$ and $R^4$ are joined together to form a ring structure having up to 20 non-hydrogen atoms as the combined substituent. More particularly, .when $R^3$ and $R^4$ are joined together, they are together selected from the group consisting of heterocyclic, substituted heterocyclic and substituted heterocyclicalkyl.

In still further more specific embodiments, R' is selected from the group consisting of alkyl, substituted alkyl, aryl, substituted aryl, cyclopentadienyl, substituted cyclopentadienyl, heteroaryl, substituted heteroaryl, heteroarylalkyl, substituted heteroarylalkyl, amino, alkoxy, saturated cyclic hydrocarbon, unsaturated cyclic hydrocarbon, heterocyclic, substituted heterocyclic, heterocyclicalkyl, substituted heterocyclicalkyl and combinations thereof. More preferably, R' is selected from the group consisting of alkyl, lower alkyl substituted alkyl, acyl substituted aLkyl, halogen substituted alkyl, alkylhalo substituted alkyl, hydroxyl substituted alkyl, phosphino substituted alkyl, alkoxy substituted alkyl, alkylamino substituted alkyl, acylamino substituted alkyl, acyloxy substituted alkyl, mercapto substituted alkyl, lower alkyl substituted aryl, acyl substituted aryl, halogen substituted aryl, alkylhalo substituted aryl, hydroxyl substituted aryl, phosphino substituted aryl, alkoxy substituted aryl, alkylamino substituted aryl, acylamino substituted aryl, acyloxy substituted aryl, mercapto substituted aryl, cyclopentadienyl, substituted cyclopentadienyl, heteroaryl, substituted heteroaryl, heteroarylalkyl, substituted heteroarylalkyl, amino, saturated cyclic hydrocarbon, unsaturated cyclic hydrocarbon, heterocyclic, substituted heterocyclic, heterocyclicalkyl, substituted heterocyclicalkyl and combinations thereof. Specific examples from which R' may be chosen are methyl, ethyl, propyl, isopropyl, benzyl, butyl, s-butyl, t-butyl, 2,4, 6-trimethylphenyl, 4-trifluoromethylphenyl, ferrocenyl, 2-pyridyl, 2-cyanophenyl, 3-cyanophenyl and 2-(diphenylphosphino)phenyl.

The ligands of this invention are prepared by the condensation reaction of a phosphine, aldehyde and amine. The corresponding precursor compounds contain the desired substituents on the phosphorus, nitrogen and carbon atoms forming the backbone of the ligands of this invention. Thus, for example, if a pyridine substituent is desirable on the carbon atom, the starting aldehyde could be pyridine-2-carboxylaldehyde. By way of further example, if the desired substituents ($R^3$ and $R^4$) on the phosphorus are both phenyl, then the starting phosphine could be diphenylphosphine. Similarly, if the desired substituents on the nitrogen atom were methyl and benzyl ($R^1$ and $R^2$), then the starting amine could be N-methylbenzylamine. The condensation reaction preferably occurs at room temperature in a polar solvent, such as tetrahydrofuran (THF). But other solvents known to those skilled the art can be used. Illustrative examples of the ligands of this invention prepared by the above method include $(tBu)(PhCH_2)NCH(Ph)P(C_6H_{11})_2$, $(PhCH_2)(CH_3)NCH(ferrocenyl)P(C_6H_{11})2$ {ferrocenyl=$^-(C_5H_4)Fe(C_5H_5)$}, $(PhCH_2)(CH_3)NCH(Ph)P(tBu)_2$, $PhN(CH_2CH_2)_2NCH(Ph)P(t-Bu)_2$, $(2-pyridineCH_2CH_2)N(CH_3)CH(Ph)P(C_6H_5)_2$, and $phCH_2)(CH_3)NCH(4-(CF_3)C_6H_4)P(C_6H_5)_2$.

Once the desired aminomethylphosphine ligand is formed, it may be reacted with a metal atom, ion or other metal precursor compound to form a metal-ligand coordination compound that may be a catalyst. The metal atom, ion or other metal precursor compound preferably combines with the ligands of this invention in a ligand exchange reaction to substitute the ligand of this invention for other ligands on the metal atom or ion, such as a chloride or methyl ligand. The metal may be chosen from any metal in the Periodic Table of Elements. In alternative embodiments, the metal is chosen from the group consisting of the transition metals of the Periodic Table of Elements. In more particular embodiments, the metal is chosen from the group consisting of Groups 3, 4, 5, 6, 7, 8, 9, 10 or 11 of the Periodic Table of Elements. Most preferred are Groups 4, 5, 6, 7, 8, 9 and 10 of the Periodic Table Elements, and specifically, Ti, Mn, Fe, Co, Ni, Cr and Pd.

The ligands of this invention. may be on a support or not. For example, the support could be any one of the R groups (i.e., R', $R^1$, $R^2$, $R^3$ or $R^4$). In that embodiment, the support may be a polymer or functionalized polymer, such as polystyrene. In the case of heterogeneous reactions, the ligands may be supported, with or without the metal coordinated (discussed below), on an organic or inorganic support. Suitable supports include silicas, aluminas, zeolites, polyethyleneglycols, polystyrenes, polyesters, polyamides, peptides and the like. Also, the ligands of this invention may be water soluble. Water solubility can be achieved via incorporation of an. appropriate functionality in any one the R groups, for example, via —$SO_3Z$, —OZ, —COOZ, etc. where Z is H, Na, K and the like.

The desired ligand is typically combined with a metal atom, ion, compound or other metal precursor compound. In many applications, the ligands of this invention will be combined with such a metal compound or precursor and the product of such combination is not determined, if a product forms. For example, the ligand may be added to a reaction vessel at the same time as the metal or metal precursor compound along with the reactants. The metal precursor compounds may be characterized by the general formula $M(D)_x$ (also referred to as $MD_x$ or M—$D_x$) where M is a metal selected from the group consisting of Groups 3, 4, 5, 6, 7, 8, 9, 10 and 11 of the Periodic Table of Elements and x is an integer appropriate for the chosen metal, such as 1, 2, 3, 4 or 5 (or higher numbers if D is neutral). In more specific embodiments, M is selected from the group consisting of Ni, Pd, Fe, Pt, Cr, Ru, Rh, Co and Ir. D is a ligand chosen from the group consisting of halide, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, hydroxy, boryl, silyl, hydrido, thio, seleno, phosphino, amino, and combinations thereof. When D is a charged ligand, D is selected from the group consisting of hydrogen, halogens, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof. When D is a neutral ligand, D is selected from the group consisting of diene, alkene, nitrile, ketone, imine, aldehyde, ether, dialkylsulfide, alkyne, carbon monoxide, isocyanide, nitrous oxide, $PA_3$, $NA_3$, $OA_2$, $SA_2$, $SeA_2$, and combinations thereof, wherein each A is independently selected from a group consisting of alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, and amino. Specific examples of suitable metal precursor compounds include $Pd(dba)_2$ (dba=dibenzylydieneacteone), $Pd_2(dba)_3$, $Pd(OAc)_2$(Ac=acetate), $PdCl_2$, $Pd(TFA)_2$, (TFA= trifluoroacetate), $(CH_3CN)_2PdCl_2$, and the like. In this context, the ligand to metal precursor compound ratio is in the range of about 0.01:1 to about 100:1, more preferably in the range of about 0.5:1 to about 20:1. The metal atom, ion or metal precursor may be supported or not. Supports may be organic or inorganic. Similar to the ligands, the support may be a D. In other embodiments, the support will not form part of the metal precursor and suitable supports include silicas, aluminas, zeolites, polyethyleneglycols, polystyrenes, polyesters, polyamides, peptides and the like. Specific examples of Pd supported metals include Pd/C, $Pd/SiO_2$, $Pd/CaCO_3$, $Pd/BaCO_3$, Pd/aluminate, Pd/aluminum oxide, Pd/polystyrene, although any of the metals listed above could replace Pd in this list, e.g., Ni/C, etc.

In other applications, the ligand will be mixed with a suitable metal precursor compound prior to or simultaneous with allowing the mixture to be contacted to the reactants. When the ligand is mixed with the metal precursor compound, a metal-ligand complex may be formed, which may be a catalyst. The ligands may be neutral or charged. When $R^1$ or $R^2$ is hydrogen, the ligand may combine with metal precursor to form coordination complexes via a ligand exchange reaction, i.e., the metals contain ligands that are exchanged for the aminomethylphosphine ligand of this invention, as those of skill in the art will recognize. When the ligands are neutral, a coordination complex may be formed without the ligand exchange reaction.

The aminomethylphosphine ligands of this invention may attach to the metal at one or more sites via one of the atoms in the backbone of the ligand (e.g., the phosphorus or nitrogen atom) or can attach via one of the substituents on the atoms in the backbone ($R^1$, $R^2$, $R^3$, $R^4$ or R'). In one preferred embodiment, the aminomethylphosphine ligands of this invention will bind to the metal via at least the nitrogen atom.

Depending on the chosen substituents, the coordination complexes of this invention may be represented by either of the general formulas:

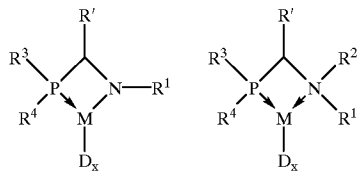

wherein $R^1$, $R^2$, R, $R^4$ and R' and M are defined as above. Additionally, the metal M may have one or more ligands D, where x is an integer from 0 to 3. Preferably, x is either 1 or 2. The ligand(s) D are selected, independently, from the group listed above, as well as alkyl, substituted alkyl, aryl, substituted aryl, arylalkyl, substituted arylalkyl, halogen, amino, silyl, germyl, hydrido, oxo, imido, sulfido, cyclopentadienyl, substituted cyclopentadienyl, alkoxy, aryloxy and combinations thereof Illustrative examples of coordination complexes are $\{(C_6H_5)_2PCH(Ph)N(CH_3)(CH_2Ph)\}NiBr_2$, $\{(C_6H_5)_2PCH(Ph)N(CH_3)(CH_2Ph)\}Pd(CH_3)Cl$, and $\{(C_6H_5)_2PCH(Ph)N(_{2,4,6}-(CH_3)_3C_6H_2)\}_2Ti(CH_2Ph)_2$.

In an alternative embodiment, one or more of the ligands D is further bonded to the aminomethylphosphine ligand via one or more of the R', $R^1$, $R^2$ $R^3$ or $R^4$ groups. In this embodiment, D is selected from the group consisting of alkyl, aryl, amino, alkoxy, aryloxy, aryloxyalkyl, heteroaryl, substituted heteroaryl, heteroarylalkyl substituted heteroarylalkyl, heterocycles substituted heterocycles and combinations thereof An illustrative example of a coordination complex within this embodiment is $[\{(C_6H_5)_2PCH(Ph)N(CH_3)CH_2CH_2N(CH_3)_2\}Pd(CH_3)]^+BAr'_4{}^-$ In another embodiment of the coordination complexes of this invention, the metal attaches to the aminomethylphosphine ligand through R' off of the carbon atom. This embodiment can be characterized by either of the following two general formulas:

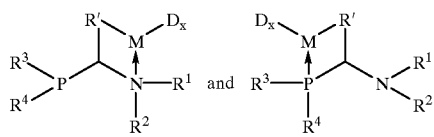

wherein $R^1$, $R^2$, $R^3$, $R^4$, R', D, M and x are as defined above and with the bond from R' to M being either dative or covalent, depending on the R' group. Illustrative examples of coordination complexes within these formula are $\{(C_6H_5)_2PCH(2\text{-pyridine})N(CH_3)(CH_2Ph)\}Pd(CH_3)Cl$ and $\{(C_6H_5)_2PCH(2\text{-pyridine})N(CH_3)(CH_2Ph)\}Pd(CH_3)N\equiv CCH_3)^+BAr'_4{}^-$.

Depending on the exact compounds chosen for $R^1$, $R^2$, $R^3$, $R^4$, R', D and M, alternative structures for the coordination complexes of this invention include:

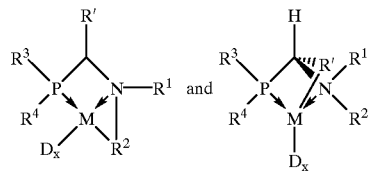

with $R^1$, $R^2$, $R^3$, $R^4$, R', D, M and x are as defined above and the bond from $R^1$ or $R^2$ groups to M being either dative or covalent.

Additional illustrative examples of the coordination complexes of this invention include $\{(CH_3)_2NCH_2CH_2N(CH_3)CH(Ph)P(C_6H_5)_2\}Pd(CH_3)(Cl)$, $\{(PhCH_2)(t\text{-Bu})NCH(Ph)P(C_6H_{11})_2\}Pd(CH_3)(Cl)$, $\{(2\text{-pyridine})CH_2CH_2N(CH_3)CH(Ph)P(C_6H_5)_2\}Pd(CH_3)(Cl)$, $\{PbN(CH_2CH_2)_2NCH(Ph)P(C_6H_5)_2\}Pd(CH_3)(Cl)$, $\{NCCH_2CH_2N(CH_3)CH(Ph)P(C_6H_5)_2\}$ $Pd(CH_3)(Cl)$, $\{(PhCH_2)(CH_3)NCH(\text{ferrocenyl})P(C_6H_{\ 1})_2\}Pd(CH_3)(Cl)$, $\{(2,4,6\text{-}(CH_3)_3C_6H_2NCH(Ph)PPh_2\}_2Ti(CH_2Ph)_2$, $\{(NCCH_2CH_2N(CH_3)CH(Ph)PPh_2\}MoCl_3$, $\{PbN(CH_2CH_2)_2NCH(Ph)PPh_2)MoCl_3$, $\{(PhCH_2)(CH_3)NCH(2\text{-pyridine})PPh_2\}FeCl_2$, $\{(PhCH_2)(CH_3)NCH(2\text{-pyridine})PPh_2\}CoCi_2$, $\{(PhCH_2)(CH_3)NCH(2\text{-pyridine})PPh_2\}NiBr_2$, and $\{(PhCH_2)(CH_3)NCH(2\text{-pyridine})P(C_6H_5)_2\}NiBr_2$ The compositions and compounds of this invention are active catalysts, but may be combined with an activator. When an activator or activating technique is used those of skill in the art may use alumoxanes, strong Lewis acids, compatible noninterfering activators and combinations of the foregoing. The foregoing activators have been taught for use with different metal complexes in the following references, which are hereby incorporated by reference in their entirety: U.S. Pat. Nos. 5,599,761, 5,616,664, 5,453, 410, 5,153,157, 5,064,802, and EP-A-277,003. Preferred activators include methylalumoxane, trimethylaluminum, $AgBF_4$, AgBPh4, $NaBAr'_4$, $H(OEt_2)_2BAr'_4$ and the like. An example of an activated complex of this invention is $\{(C_6H_{11})_2PCH(Ph)N(CH_3)(CH_2Ph)\}Pd(CH_3)(N\equiv CCH_3)^+BAr'_4{}^-$ where Ar is $3,5\text{-}(CF_3)_2(C_6H_3)$. Ratios of neutral complex to activator are on the order of 1 to 1000 to 1000 to 1. More specifically, a ratio of about 1 to 1 is preferred. A scavenger can also be used with this invention. Scavengers useful herein include metal complexes, alumoxanes, aluminum alkyls and the like.

The catalyst compositions and metal complexes of this invention catalyze reactions that include activation of and/or formation of H—Si, H—H, H—N, H—O, H—P, H—S, C—H, C—C, C=C, C≡C, C—halogen, C—N, C—O, C—S, C—P, and C—Si bonds. Specifically, such reactions include carbonylation, hydroformylation, hydroxycarbonylation, hydrocarbonylation, hydroesterification, hydrogenation, transfer hydrogenation, hydrosilylation, hydroboration, hydroamination, epoxidation, aziridation, reductive amination, C—H activation, insertion, C—H activation-insertion, C—H activation-substitution, C-halogen activation, C-halogen activation-substitution, C-halogen activation-insertion, cyclopropanation, alkene metathesis, alkene oligomerization, alkene polymerization, alkyne oligomerization, alkyne polymerization, co-polymerization, CO-alkene co-oligomerizatiqn, CO-alkene co-polymerization, CO-alkyne co-oligomerization and CO-alkyne co-polymerization. These reactions may occur at previously known conditions (or possibly novel conditions). Moreover, these reactions may be homogeneous or heterogeneous.

The catalysts herein may be used to polymerize ethylenically or acetylenically unsaturated monomers having from 2 to 20 carbon atoms either alone or in combination. Monomers include $C_2$ to $C_{20}$ α-olefins such as ethylene, propylene, 1-butene, 1-hexene, 1-octene, 4-methyl-l-pentene, styrene and mixtures thereof. Polymerization can be carried out in the Ziegler-Natta or Kaminsky-Sinn methodology, including temperatures of from 0° C. to 400° C. and pressures from atmospheric to 3000 atmospheres. Suspension, solution, slurry, gas phase or high-pressure polymerization processes may be employed with the catalysts and compounds of this invention. Such processes can be run in a batch or continuous mode. Examples of such processes are well known in the art. A support for the catalyst may be employed, which may be alumina, silica or a polymers support. Methods for the preparation of supported catalysts are known in the art. Slurry, suspension, solution and high-pressure processes use a suitable solvent as known to those skilled in the art.

The compounds and catalysts of this invention usefully polymerize fanctionalized monomers, such as acetates and acrylates. Novel polymers, copolymers or interpolymers may be formed having unique physical and melt flow properties. Such novel polymers can be employed alone or with other polymers in a blend to form products that may be molded, cast, extruded or spun. End uses for the polymers made with the catalysts of this invention include films for packaging, trash bags, foams, coatings, insulating devices and household items. Also, such finctionalized polymers are useful as solid supports for organometallic or chemical synthesis processes.

The catalyst compositions and metal complexes of this invention are also useful for many metal-catalyzed reactions, particularly for aryl amination or Suzuki cross-coupling reactions with aryl chlorides. For the details of aryl animation reactions, see U.S. Pat. No. 5,576,460, incorporated herein by reference. In general, this invention may be effectively employed for metal-catalyzed coupling of organometallic reagents with organic electrophiles; metal-catalyzed coupling of organometallic reagents with organic halides; metal-catalyzed coupling of organometallic reagents with aryl halides and vinyl halides; and metal-catalyzed coupling of organometallic reagents with aryl chlorides. In particular, the following reactions can be effectively performed with this invention: aryl-aryl or biaryl coupling reactions, including coupling of aryl boron reagents (aryl boronic acid and esters) with aryl halides including aryl chlorides, aryl triflates, aryl tosylates, aryl mesylates (Suzuki coupling); coupling of aryl zinc reagents with the compounds as above; coupling of aryl magnesium reagents with the compounds as above; coupling of aryl tin reagents with the compounds as above; and coupling of aryl metal reagents with the compounds as above. Those of skill in the art will recognize that this list can be repeated by simply substituting heteroaryl for aryl without departing from the scope of this invention. Additional reactions that can be effectively performed with this invention include vinyl-aryl coupling reactions such as the coupling of vinyl metal reagents with the compounds as above, coupling of vinyl aluminate reagents with the compounds as above, coupling of vinyl cuprate reagents with the compounds as above, coupling of vinyl zirconium reagents with the compounds as above; and the coupling of vinyl boron reagents with the compounds as above. Still further, reactions that can be effectively performed with this invention include reactions which involve oxidative addition, transmetallation and reductive elimination sequence or oxidative addition, insertion or beta-hydride elimnation sequence in the catalytic cycle, including Heck reactions that involve metal-catalyzed olefination of aryl halides including chloride, aryl mesylates, tosylates, aryl triflates. Other reaction examples, include Sonogashira, cyanation, aryl amination, Stille coupling, Castro-Stephens, and hydrogenations.

To carry out one process of this invention for one type of reaction, a first aromatic compound, a second aromatic compound, a base, a catalytic amount of metal precursor and a catalytic amount of the ligand are added to an inert solvent or inert solvent mixture. In a batch methodology, this mixture is stirred at a temperature of from 0° C. to 200° C., preferably at from 30° C. to 1 70° C., particularly preferably at from 50° C. to 150° C., most particularly preferably at from 60° C. to 120° C., for a period of from 5 minutes to 100 hours, preferably from 15 minutes to 70 hours, particularly preferably from ½ hour to 50 hours, most particularly preferably from 1 hour to 30 hours. After the reaction is complete, the catalyst may be obtained as solid and separated off by filtration. The crude product is freed of the solvent or the solvents and is subsequently purified by methods known to those skilled in the art and matched to the respective product, e.g. by recrystallization, distillation, sublimation, zone melting, melt crystallization or chromatography.

Solvents suitable for the process of the invention are, for example, ethers (e.g., diethyl ether, dimethoxymethane, diethylene glycol, dimethyl ether, tetrahydroflran, dioxane, diisopropyl ether, tert-butyl methyl ether), hydrocarbons (e.g., hexane, iso-hexane, heptane, cyclohexane, benzene, toluene, xylene), alcohols (e.g., methanol, ethanol, 1-propanol, 2-propanol, ethylene glycol, 1-butanol, 2-butanol, tert-butanol), ketones (e.g., acetone, ethyl methyl ketone, iso-butyl methyl ketone), amides (e.g., dimethylformamide, dimethylacetamide, N-methylpyrrolidone), nitriles (e.g., acetonitrile, propionitrile, butyronitrile), water and mixtures thereof. Particularly preferred solvents are ethers (e.g., dimethoxyethane, tetrahydrofuran), hydrocarbons (e.g., cyclohexane, benzene, toluene, xylene), alcohols (e.g., ethanol, 1-propanol, 2-propanol), water and combinations thereof. Most particularly preferred are dimethoxyethane, benzene, toluene, xylene, dioxane, ethanol, water and combinations thereof.

Bases which are useful in the process of the invention are alkali metal and alkaline earth metal hydroxides, alkali metal and alkaline earth metal carbonates, alkali metal hydrogen carbonates, alkali metal and alkaline earth metal acetates, alkali metal and alkaline earth metal alkoxides, alkali metal and alkaline earth metal phosphates, primary, secondary and tertiary amines, alkali metal and alkaline earth fluorides, and ammonium fluorides. Particularly preferred are alkali metal and alkaline earth metal phosphates, alkali metal and alkaline earth metal carbonates, alkali metal hydrogen carbonates, alkali metal and alkaline earth fluorides, and ammonium fluorides. Most particularly preferred are alkali metal phosphates, such as potassium phosphate. The base is preferably used in the process of the invention in an amount of from about 1 to about 1000 mol %, particularly preferably from about 50 to about 500 mol %, very particularly preferably from about 100 to about 400 mol %, in particular from about 150 to about 300 mol %, based on the aromatic boronic acid.

The metal precursor used is as described above and may be added to the process along with the reactants. The metal portion of the catalyst (metal precursor or metal complex) is used in the process of this invention in a proportion of from about 0.0001 to about 10 mol %, preferably from about 0.1 to about 5 mol %, particularly preferably from about 0.5 to about 3 mol %, most particularly preferably from about 1.0 to about 1.5 mol %, based on the second aromatic compound. The ancillary ligand is used in the process in a proportion of from about 0.0001 to about 20 mol %, preferably from about 0.2 to about 15 mol %, particularly preferably from about 0.5 to about 10 mol %, most particularly preferably from about 1 to about 6 mol %, based on the second aromatic compound. These amounts may be combined to give metal precursor to ligand ratios useful in the process. It is also possible, if desired, to use mixtures of two or more different ligands.

The first aromatic compounds for the process may be characterized by either of the general formulas:

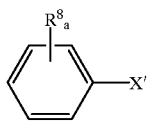

XIII

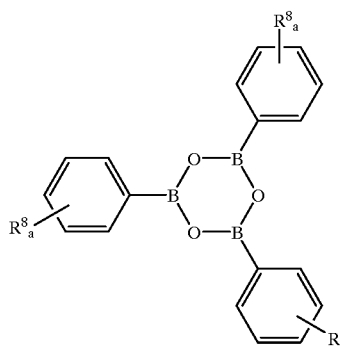

XIV where $R^8$ is selected from the group consisting of hydrogen, alklyi, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof, a is 0, 1, 2, 3, 4 or 5 and optionally two or more $R^8$ groups are joined together in a ring structure; X' is selected from the group consisting of $BR^{10}_2$, $B(OR^{10})_2$, $MgQ^1$, $ZnQ^1$, $CuQ^1$, $SiR^{10}_3$ $SnR^{10}_3$ or Li, wherein each $R^{10}$ is independently selected from the group consisting of hydrogen, alkyl, substituted alcyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; and $Q^1$ is selected from the group consisting of Cl, Br, I or F. See also U.S. Pat. No. 5,756,804, incorporated herein by reference for other, similar formulas. Specific boronic acids that fit this definition of first aromatic compounds are listed in Table 1, below.

The second aromatic compounds for the process of the invention those of the formula:

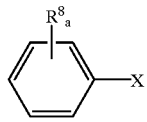

where X is Br, Cl, F, I, tosylates, triflates, or $N_2^+$ and $R^9$ is selected from the group consisting of hydrogen, alkyl, substituted alkyl, cycloaliyl, substituted cycloalkyl, heteroalkyl, heterocycloalkyl, substituted heterocycloallyl, aryl, substituted aryl, heteroaryl, substituted heteroaryl, alkoxy, aryloxy, silyl, boryl, phosphino, amino, thio, seleno, and combinations thereof; and a is 0, 1, 2, 3, 4 or 5. Optionally two or more $R^9$ groups are joined together in a ring structure. Preferable, $R^9$ is selected from the group consisting of methyl, ethyl, methoxy, —CN and —$CF_3$. See also U.S. Pat. No. 5,756,804, incorporated herein by reference for other, similar formulas. Specific compounds that meet fit within the scope of the second aromatic compounds are listed in Table 1.

Products of the process of the invention are polycyclic aromatic compounds having a aryl—aryl bond, having the general structure:

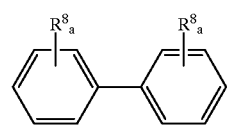

The products are also suitable as precursors for pharmaceuticals, cosmetics, fingicides, herbicides, insecticides, dyes, detergents and polymers, including additives for the same.

The ligands, metal-ligand complexes and compositions of this invention can be prepared and tested for catalytic activity in one or more of the above reactions in a combinatorial fashion. Combinatorial chemistry generally involves the parallel or rapid serial synthesis and/or screening or characterization of compounds and compositions of matter. U.S. Pat. No. 5,776,359 generally discloses combinatorial methods and WO 98/03521 discloses combinatorial methods for organometallic chemistry, both of which are incorporated herein by reference. In this regard, the ligands, complexes or compositions may be prepared and/or tested in rapid serial and/or parallel fashion, e.g., in an array format. When prepared in an array format, for example, the ligands may be take the form of an array comprising a plurality of compounds wherein each compound can be characterized by the above general formulas.

In such a combinatorial array, typically each of the plurality of compounds has a different composition and each compound is at a selected region on a substrate such that each compound is isolated from the other compounds. This isolation can take many forms, typically depending on the substrate used. If a flat substrate is used, there may simply be sufficient space between regions so that there cannot be interdiffusion between compounds. As another example, the substrate can be a microtiter or similar plate having wells so that each compound is in a region separated from other compounds in other regions by a physical barrier.

The array typically comprises at least 10 ligands, compounds, complexes or compositions each having a different chemical formula, meaning that there must be at least one different atom or bond differentiating the plurality in the array. In other embodiments, there are at least 25 compounds, complexes or compositions on or in the substrate each having a different chemical formula In still other embodiments, there are at least 50 or 96 or 124 ligands, compounds, complexes or compositions on or in the substrate each having a different chemical formula. Because of the manner of forming combinatorial arrays, it may be that each compound, complex or composition is not pure. Typically, each compound in the plurality of compounds is at least 50% pure within its region. In other embodiments, each element of the array comprises the composition of matter described above, comprising the ligand and a metal precursor. The same array discussion above applies to arrays of this type. In still other embodiments, each element of the array is a metal-ligand complex defined above. The same array discussion above applies to arrays of this type.

EXAMPLES

Unless otherwise noted, all manipulations were conducted under an atmosphere of dry, deoxygenated nitrogen in a Vacuum Atmospheres glovebox. Hexane, diethyl ether, THF, and toluene were sparged with nitrogen and passed though columns of activated $Al_2O_3$ and CU-0226S (Engelhart; a commerically available oxygen scavenger). Dichloromethane was sparged with nitrogen and passed though activated alumina. Dicyclohexylphosphine was purchased from Strem; all other library reagents were purchased from Aldrich in the highest available purity and used without further purification. NMR spectra were recorded on a Bruker 300 MHz spectrometer. $^1H$ and $^3C$ chemical shifts were referenced relative to residual protio solvent peaks and $^{13}C$ peaks, respectively; $^{31}P$ chemical shifts were referenced to an external standard (85% $H_3PO_4$). Elemental analyses were performed by QTI (Whitehouse, N.J.). (COD)PdMeCl was prepared from (COD)PdCl$_2$ (Strem) and Me$_4$Sn in $CH_2Cl_2$. NaBAr'$_4$ and H(OEt$_2$)$_2$BAr'$_4$ were prepared by reported procedures (Brookhart et al, Organometallics, 1992, 11, 3920). NMR solvents were purchased from Cambridge Isotopes, sparged with nitrogen and stored over 4A molecular sieves.

EXAMPLES 1–10

Examples 1–10 are examples of the preparation of aminomethylphosphine ligands (also referred to as "PCN" or generically $R^1R^2NCHR'PR^3R^4$). Each of these examples uses the same synthesis route, called method A, which is: In a glovebox, $R^3R^4PH$ (1.0–1.2 eq.), R'CHO (1.0–1.3 eq.), and $R^1R^2NH$ (1.0–1.3 eq.) were combined in THF (5–50 mL). The mixture was allowed to stir overnight at room temperature. THF was removed in vacuo, and the resulting oil or solid was dissolved in a minimal amount of pentane and recrystallized at −35° C. and dried in vacuo. Specific details for Examples 1–10 are as follows:

Example 1:

(PhCH$_2$)(CH$_3$)NCH(Ph)P(C$_6$H$_{11}$)$_2$. The reaction was set up as described in method A using 2.00 mL (C$_6$H$_{11}$)$_2$PH (9.90 mmol), 1.20 mL PhCHO (12.2 mmol), 1.30 mL (PhCH$_2$)(CH$_3$)NH (10.1 mmol) and 30 mL THF. 3.30 g (83%) of (PhCH$_2$)(CH$_3$)NCH(Ph)P(C$_6$H$_{11}$)$_2$ was obtained as a colorless solid. $^{31}P$ NMR (CDCl$_3$) δ −3.61

Example 2:

(PhCH$_2$)(CH$_3$)NCH(Ph)P(C$_6$H$_5$)$_2$. The reaction was set up as described in method A, using 2.00 mL (C$_6$H$_5$)$_2$PH (11.5 mmol), 1.20 mL PhCHO (12.2 mmol), 1.30 mL (PhCH$_2$)(CH$_3$)NH (10.1 mmol) and 30 mL THF. Upon isolation of the crude product, a colorless solid was obtained which was washed with pentane (10 mL) and dried (2.97 grams). The pentane washings were cooled to −40° C. and an additional 0.66 gram of (PhCH$_2$)(CH$_3$)NCH(Ph)P(C$_6$H$_5$)$_2$ was collected. Total yield=3.63 g=77%. $^{31}P$ NR (CDCl$_3$) δ −17.15

Example 3:

(t-Bu)NHCH(Ph)P(C$_6$H$_5$)$_2$. In a modification of method A, a large excess of t-BuNH$_2$ was used; specifically 2.00 mL (C$_6$H$_{11}$)$_2$PH (11.5 mmol), 1.18 mL PhCHO (12.0 mmol), 3.0 mL (t-BuNH$_2$ (28.2 mmol).) and 20 mL THF were used. A colorless solid was obtained which was recrystallized from pentane (yield=2.97 g; 73%).

Example 4:

(2,4,6-(CH$_3$)$_3$C$_6$H$_2$)NHCH(Ph)P(C$_6$H$_5$)$_2$: The reaction was set up as described in method A, using 0.350 mL (C$_6$H$_5$)$_2$PH (2.0 mmol), 0.200 mL PhCHO (2.0 mmol), 0.280 mL (2,4,6-(CH$_3$)$_3$C$_6$H$_2$)NH$_2$ (2.0 mmol) and 5 mL THF. Upon recrystallization, a colorless solid was obtained (yield=495 mg, 58%). $^{31}P$ NMR (CDCl$_3$) δ 3.81

Example 5:

(CH$_3$)$_2$NCH$_2$CH$_2$N(CH$_3$)CH(Ph)P(C$_6$H$_5$)$_2$. The reaction was set up as described in method A, using 0.350 mL (C$_6$H$_5$)$_2$PH (2.0 mmol), 0.210 mL PhCHO (2.1 mmol), 0.253 (CH$_3$)$_2$NCH$_2$CH$_2$NH(CH$_3$) (2.0 mmol) and 5mL THF. A clear colorless oil resulted upon removal of THF; this oil was>95% pure by $^1H$ NMR spectroscopy and was used without farther purification (yield=504 mg, 67%).

Example 6:

(PhCH$_2$)(CH$_3$)NCH(2-pyridine)P(C$_6$H$_{11}$)$_2$. In a modification of method A, molecular sieves (4A) were added to the reaction mixture with 0.400 mL (C$_6$H$_{11}$)$_2$PH (2.0 mmol), 0.190 mL pyridine-2-carboxaldehyde (2.0 mmol), 0.260 mL (PhCH$_2$)(CH$_3$)NH (2.0 mmol) and 5 mL THF. After 24 hours, the reaction mixture was filtered and THF was removed in vacuo. The resulting pink oil was recrystallized from pentane at −35° C., yielding a pink waxy solid (yield= 527 mg; 65%). $^{31}P$ NMR (CDCl$_3$) δ −1.57.

Example 7:

(PhCH$_2$)(CH$_3$)NCH(2-pyridine)P(C$_6$H$_5$)$_2$. In a modification of method A, molecular sieves (4A) were added to the reaction mixture with 0.700 mL (C$_6$H$_5$)$_2$PH (4.0 mmol), 0.380 mL pyridine-2-carboxaldehyde (4.0 mmol), 0.520 mL (PhCH$_2$)(CH$_3$)NH (4.0 nimol) and 5 mL THF. After 24 hours, the reaction mixture was filtered and THF was removed in vacuo. The resulting pink oil was recrystallized from pentane at −35° C., yielding a pink waxy solid (yield= 683 mg; 43%). $^{31}P$ NMR (CDCl$_3$) δ −16.84.

Example 8:

PhN(CH$_2$CH$_2$)$_2$NCH(Ph)P(C$_6$H$_{11}$)$_2$. The reaction was set up as described in method, using 2.01 g (C$_6$H$_{11}$)$_2$PH (10 mmol), 1.20 mL PhCHO (12.3 mmol), 1.52 g PhN(CH$_2$CH$_2$)$_2$NH (10.3 mmol) and 15 mL THF. After 24 hours, a colorless crystalline solid had formed in the reaction mixture. The solid was washed with pentane and dried in vacuo (yield=3.02 g; 70%). $^{31}P$ NMR (CDCl$_3$) δ −1.57.

Example 9:

PhN(CH$_2$CH$_2$)$_2$NCH(Ph)P(C$_6$H$_5$)$_2$. The reaction was set up as described in method A, using 1.50 mL (C$_6$H$_5$)$_2$PH (8.6 mmol), 1.20 mL PhCHO (12.3 mmol), 1.52 g PhN(CH$_2$CH$_2$)$_2$NH (10.3 mmol) and 10 mL THF. After 24 hours, the reaction mixture was concentrated to 5 mL, at which point crystals began to form. Pentane (10 mL) was added and the precipitate was collected, washed with pentane and dried. A second crop of crystals was collected by cooling the filtrate to −35° C. (combined yield=2.93 g; 98%).

Example 10:

$(NCCH_2CH_2)(CH_3)NCH(Ph)P(C_6H_5)_2$. The reaction was set up as described in method A, using 3.50 mL $(C_6H_5)_2PH$ (20.1 mmol), 2.30 mL PhCHO (23.4 mmol), 2.00 mL $NCCH_2CH_2NH(CH_3)$ (21.4 mmol) and 10 mL THF. Upon removal of THF, a pale yellow oil was obtained. The oil was washed with 10 mL pentane, which caused it to solidify into a waxy off-white solid. The solid was dried in vacuo (yield=6.02 g; 86%).

EXAMPLES 11–13

Examples 11–13 are examples of the preparation of coordination complexes of certain PCN ligands with $NiBr_2$. Examples 11–13 used the following general synthesis procedure, called method B, which is: In a glovebox, solid $NiBr_2(DME)$ (1.0 eq.) and the PNC ligand (1.0–1.2 eq.) were combined. $CH_2Cl_2$ (5–20 mL) was added and the resulting generally red mixture was allowed to stir overnight. The mixture was then filtered and $CH_2Cl_2$ was removed in vacuo, yielding a generally dark red solid, which was washed with pentane and dried. Yields and specific details are as follows:

Example 11:

$\{(PhCH_2)(CH_3)NCH(2\text{-pyridine})P(C_6H_5)_2\}NiBr_2$. Using method B, $\{(PhCH_2)(CH_3)NCH(2\text{-pyridine})P(C_6H_5)_2\}NiBr_2$ was prepared from $(PhCH_2)(CH_3)NCH(2\text{-pyridine})P(C_6H_5)_2$ (212 mg, 0.54 mmol) and $NiBr_2(DME)$ (135 mg, 0.44 mmol). The dark red product was recrystallized from $CH_2Cl_2$/pentane at −35° C. (185 mg; 68%). Anal: Calc. for $C_{26}H_{25}N_2Br_2NiP$: C; 53.47, H; 4.31, N, 4.80. Found: C, 55.49, H; 4.74, N; 4.89.

Example 12:

$\{(PhCH_2)(CH_3)NCH(2\text{-pyridine})P(C_6H_{11})_2\}NiBr_2$. Using method B, $(PhCH_2)(CH_3)NCH(2\text{-pyridine})P(C_6H_{11})_2\}NiBr_2$ was prepared from $(PhCH_2)(CH_3)NCH(2\text{-pyridine})P(C_6H_{11})_2$(161 mg, 0.40 mmol) and $NiBr_2(DME)$ (125 mg, 0.40 mmol). A dark red microcrystalline powder was obtained. (95 mg, 38%) Anal: Calc. for $C_{26}H_{37}N_2Br_2NiP$: C; 51.66, H; 5.73, N; 4.30. Found: 51.41, H; 6.27, N, 4.25.

Example 13:

$\{(PhCH_2)(CH_3)NCH(Ph)P(C_6H_{11})_2\}NiBr_2$. Using method B, $\{(PhCH_2)(CH_3)NCH(Ph)P(C_6H_{11})_2\}NiBr_2$ was prepared from $(PhCH_2)(CH_3)NCH(Ph)P(C_6H_{11})_2$ (417 mg, 1.02 mmol) and $NiBr_2(DME)$ (312 mg, 1.01 mmol). The pink-red product was recrystalized from $Et_2O$/pentane at −35° C. (308 mg; 49%).

EXAMPLES 14–17

Examples 14–17 are examples of the preparation of coordination complexes of certain PCN ligands with $Pd(CH_3)(Cl)$. Each of these examples used the same general synthesis procedure, called method C, which is: In a glovebox, solid $(COD)Pd(CH_3)(Cl)$ (1.0–1.1 eq.) and the PCN ligand (1.0–1.1 eq.) were combined. $Et_2O$ (5–50 mL) was added. After 10–30 minutes, a powder precipitated from solution. The powder was collected, washed with $Et_2O$ and dried in vacuo. Specific details for each example are as follows:

Example 14:

$\{(PhCH_2)(CH_3)NCH(Ph)P(C_6H_{11})_2\}Pd(CH_3)(Cl)$. Following method C, $\{(PhCH_2)(CH_3)NCH(Ph)P(C_6H_{11})_2\}Pd(CH_3)(Cl)$ was prepared from $(COD)Pd(CH_3)(Cl)$ (569 mg, 2.15 mmol) and $(PhCH_2)(CH_3)NCH(Ph)P(C_6H_{11})_2$(825 mg, 2.02 mmol) in 40 mL of $Et_2O$. (yield: 810 mg, 72%) Anal: Calc'd for $C_{28}H_{41}NClPPd$: C; 59.78, H; 7.31, N; 2.48. Found: C; 60.22, H; 7.34, N, 2.33.

Example 15:

$\{(PhCH_2)(CH_3)NCH(Ph)P(C_6H_5)_2\}Pd(CH_3)(Cl)$. Following method C, $\{(PhCH_2)(CH_3)NCH(Ph)P(C_6H_5)_2\}Pd(CH_3)(Cl)$ was prepared from $(COD)Pd(CH_3)(Cl)$ (264 mg, 1.0 mmol) and $(PhCH_2)(CH_3)NCH(Ph)P(C_6H_5)_2$ (389 mg, 1.0 mmol) in 15 mL of $Et_2O$. (yield: 454 mg, 84%) Anal: Calc'd for $C_{28}H_{29}NClPPd$: C; 60.88, H; 5.29, N; 2.54. Found: C; 60.65, H; 5.49, N, 2.16.

Example 16:

$\{(PhCH_2)(CH_3)NCH(2\text{-pyridine})P(C_6H_{11})_2\}Pd(CH_3)(Cl)$. Following method C, $\{(PhCH_2)(CH_3)NCH(2\text{-pyridine})P(C_6H_{11})_2\}Pd(CH_3)(Cl)$ was prepared from $(COD)Pd(CH_3)(Cl)$ (31 mg, 0.12 mmol) and $(PhCH_2)(CH_3)NCH(2\text{-pyridine})P(C_6H_{11})_2$ (51 mg, 0.12 mmol) in 5 mL of $Et_2O$. (yield: 68 mg, 96%)

Example 17:

$\{(PhCH_2)(CH_3)NCH(2\text{-pyridine})P(C_6H_5)_2\}Pd(CH_3)(Cl)$. Following a modified method C, $\{(PhCH_2)(CH_3)NCH(2\text{-pyridine})P(C_6H_5)_2\}Pd(CH_3)(Cl)$ was prepared from $(COD)Pd(CH_3)(Cl)$ (105 mg, 0.40 mmol) and $(PhCH_2)(CH_3)NCH(2\text{-pyridine})P(C_6H_5)_2$ (156 mg, 0.39 mmol) in 5 mL of toluene. A beige solid precipitated from solution and was collected, washed with pentane and dried in vacuo. (yield: 194 mg; 90%) Anal: Calc'd for $C_{27}H_{28}N_2ClPPd$: C; 58.60, H; 5.10, N; 5.06. Found: C; 59.39, H; 5.25, N, 4.78.

EXAMPLES 18–21:

Examples 18–21 are examples of the preparation of an active polymerization catalyst that can be characterized by the general formula $\{(PCN)Pd(CH_3)(NCCH_3)\}^+\{BAr'_4\}^-$ (where Ar' is $3,5\text{-}(CF_3)_2(C_6H_3)$). Example 18 used the complex of Example 14, Example 19 used the complex of Example 15, Example 20 used the complex of Example 16 and Example 21 used the complex of Example 17. Examples 18–21 each used the following preparation: In a glovebox, $(PCN)Pd(CH_3)(Cl)$ (1.0 equiv), $NaBAr'_4$ (1.0–1.1 equiv.) and $CH_3CN$ (1–100 eq.) were combined. $CH_2Cl_2$ (1–50 mL) was added and the mixture was allowed to stir for 1 hour. The mixture was then filtered, and $CH_2Cl_2$ and $CH_3CN$ were removed in vacuo, leaving a glassy solid. The solid was washed with pentane and dried in vacuo. Example 18 resulted in the formation of $\{(PhCH_2)(CH_3)NCH(Ph)P(C_6H_{11})_2Pd(CH_3)(NCCH_3)\}^+$ $\{BAr'_4\}^-$. Example 19 resulted in the formation of $\{(PhCH_2)(CH_3)NCH(Ph)P(C_6H_5)_2Pd(CH_3)(NCCH_3)\}^+$ $\{BAr'_4\}^-$. Example 20 resulted in the formation of $\{(PhCH_2)(CH_3)NCH(2\text{-pyridine})P(C_6H_{11})_2Pd(CH_3)(NCCH_3)\}^+$ $\{BAr'_4\}^-$. Example 21 resulted in the formation of $\{(PhCH_2)(CH_3)NCH(2\text{-pyridine})P(C_6H_5)_2Pd(CH_3)(NCCH_3)\}^+$ $\{BAr'_4\}^-$.

Other complexes prepared by the same procedure described for Examples 18–21 include $\{(CH_3)_2NCH_2CH_2N(CH_3)CH(Ph)P(C_6H_5)_2\}Pd(CH_3)(CH_3CN)\}^+$ $\{BAr'_4\}^-$, $\{(PhCH_2)(t\text{-Bu})NCH(Ph)P(C_6H_{11})_2\}Pd(CH_3)(CH_3CN)\}$ $\{BAr'4\}^-$, $\{(2\text{-pyridine}) CH_2CH_2N(CH_3)CH(Ph)P(C_6H_5)_2\}Pd(CH_3)(CH_3CN)\}^+$ $\{BAr'_4\}^-$, $\{PhN(CH_2CH_2)_2NCH(Ph)P(C_6H_5)_2\} Pd(CH_3)(CH_3CN)\}^+$ $\{BAr'_4\}^-$, $\{NCCH_2CH_2N(CH_3)CH(Ph)P(C_6H_5)_2)Pd(CH_3)(CH_3CN)$ $\}^+$ $\{BAr'_4\}^-$;, and $\{(PhCH_2)(CH_3)NCH(ferrocenyl)P(C_6H_{11})_2\}Pd(CH_3)(CH_3CN)\}^+$ $\{BAr'_4\}^-$.

EXAMPLES 22–117:

Examples 22–117 are ligand synthesis examples. The syntheses were carried out in parallel using combinatorial chemistry techniques, as follows and using the chemicals set in Table 1, below. Each synthesis was set up by preparing 1.0 M solutions of the starting solutions in THF. A 96 well microtiter plate fitted with fritted glass wells was used. 4 A molecular sieves (appx. 40 mg/well) were dispensed into the plate using a solid dispening plate. Each synthesis was carried out by placing about 500 μL of THF into each well of the microtiter plate, and then 100 μL of the phosphine solution (0.1 mmol) and 110 μL of the aldehyde and amine solutions (0.11 mmol) were added. The top of the microtiter plate was then covered with a sheet of TEFLON, a sheet of butyl rubber and a sheet of latex and then clamped to seal the microtiter plate. The plate assembly was then shaken gently overnight. The microtiter plate was then disassembled from the clamp assembly and transferred to a filter block. Fitrate from each well was collected in a 96 well microtiter plate, and each well of the reaction vessel was washed with 300 μL of THF. The solvent was then removed from the microtiter plate by blowing a steady stream of nitrogen and the microtiter plate was then dried in vacuo by placing it in the glovebox antechamber for about two hours.

Examples 22–117 used the following starting materials:

In 37 wells, partial or complete crystallization was observed after THF was removed. In 10 cases, the aminomethylphosphine ligands had been previously prepared by traditional solution chemistry and in all cases the morphology (crystalline or liquid) of those ligands prepared in the library matched that of the purified compounds. Selected elements of the library were then characterized by $^{31}$P NMR and were found to be the desired ligand. Use of these starting materials formed the following ligands:

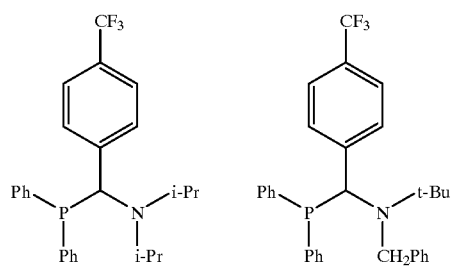

Starting Material Matrix for Examples 22-117

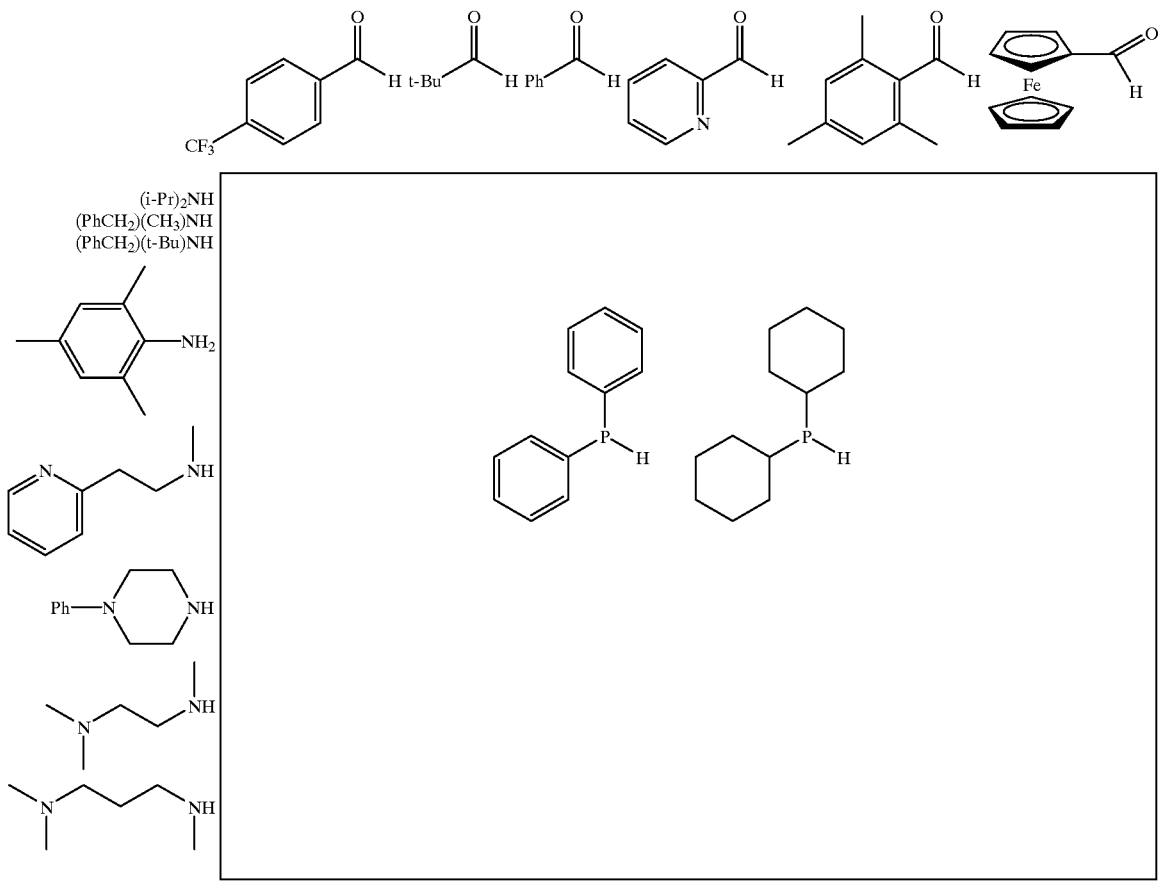

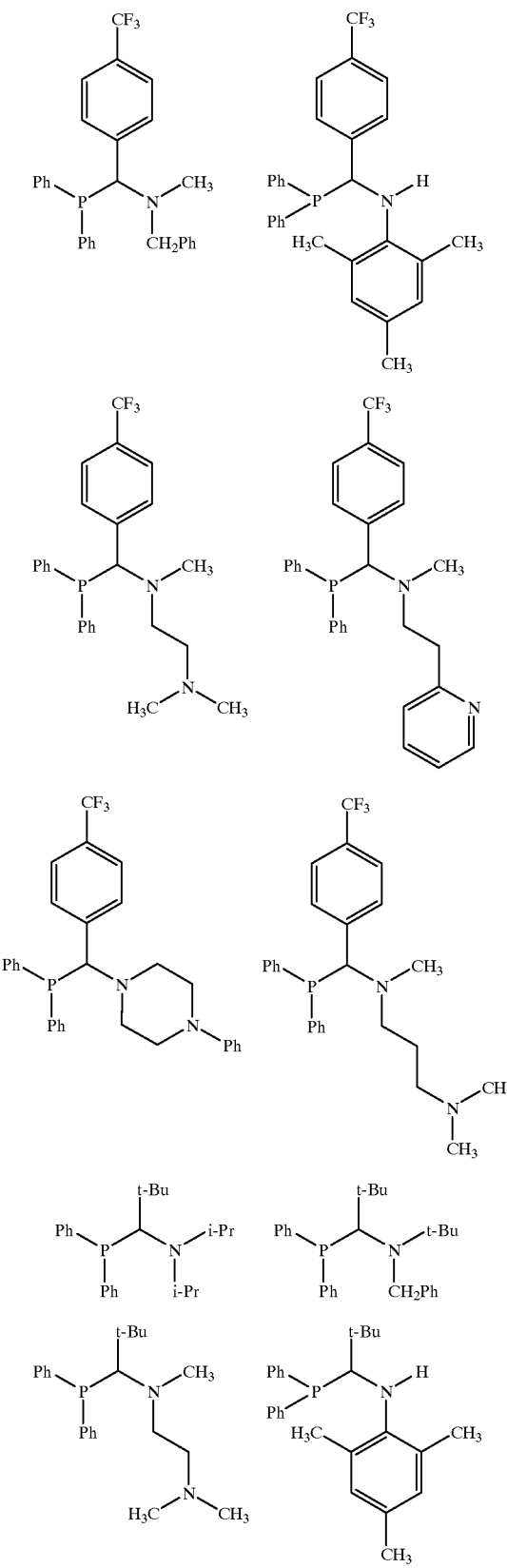
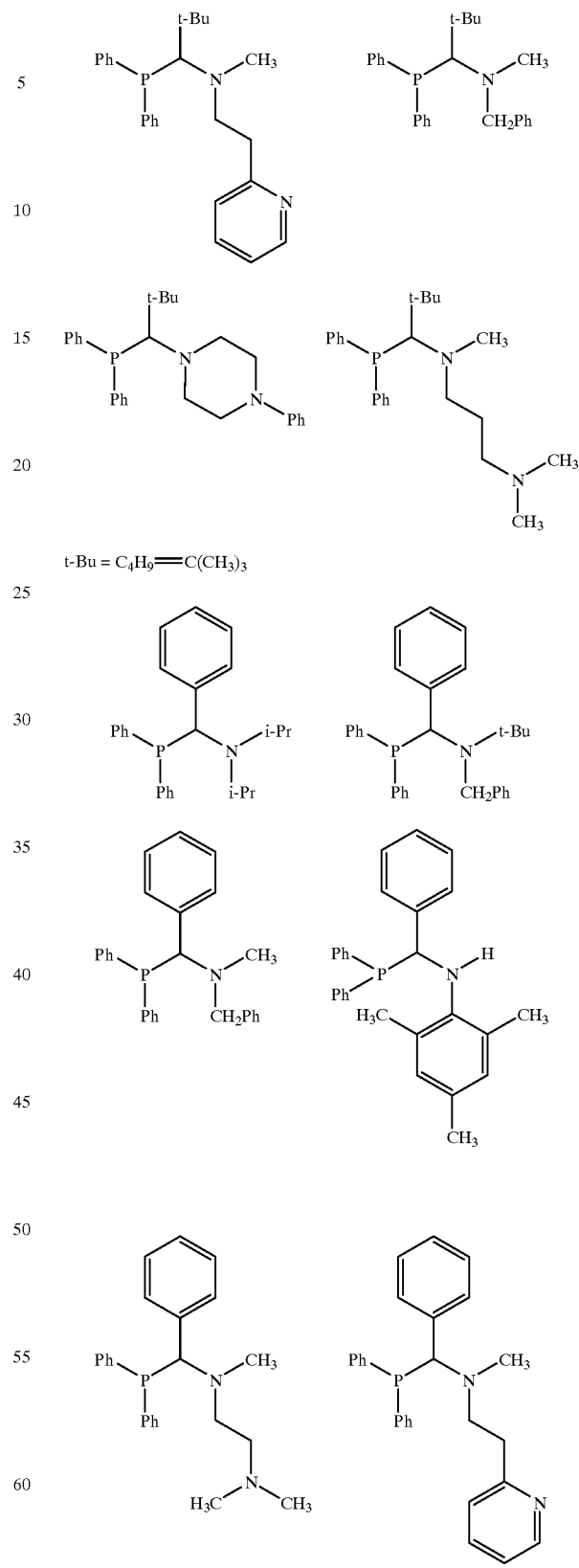
t-Bu = C₄H₉ = C(CH₃)₃

-continued
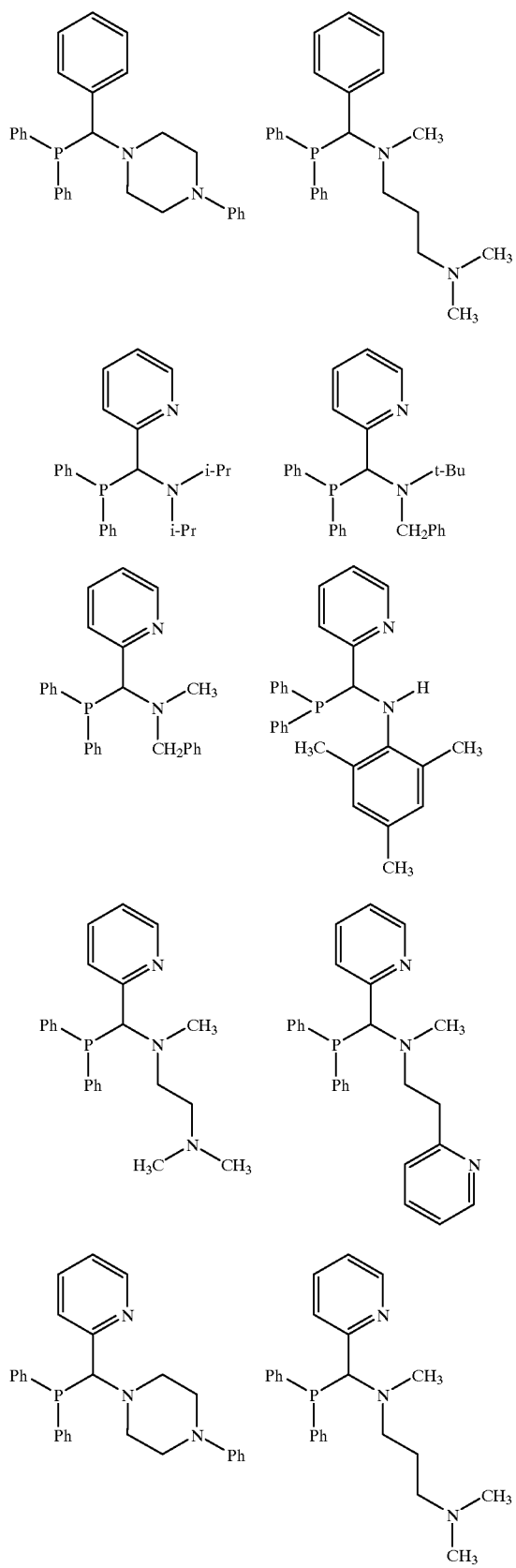
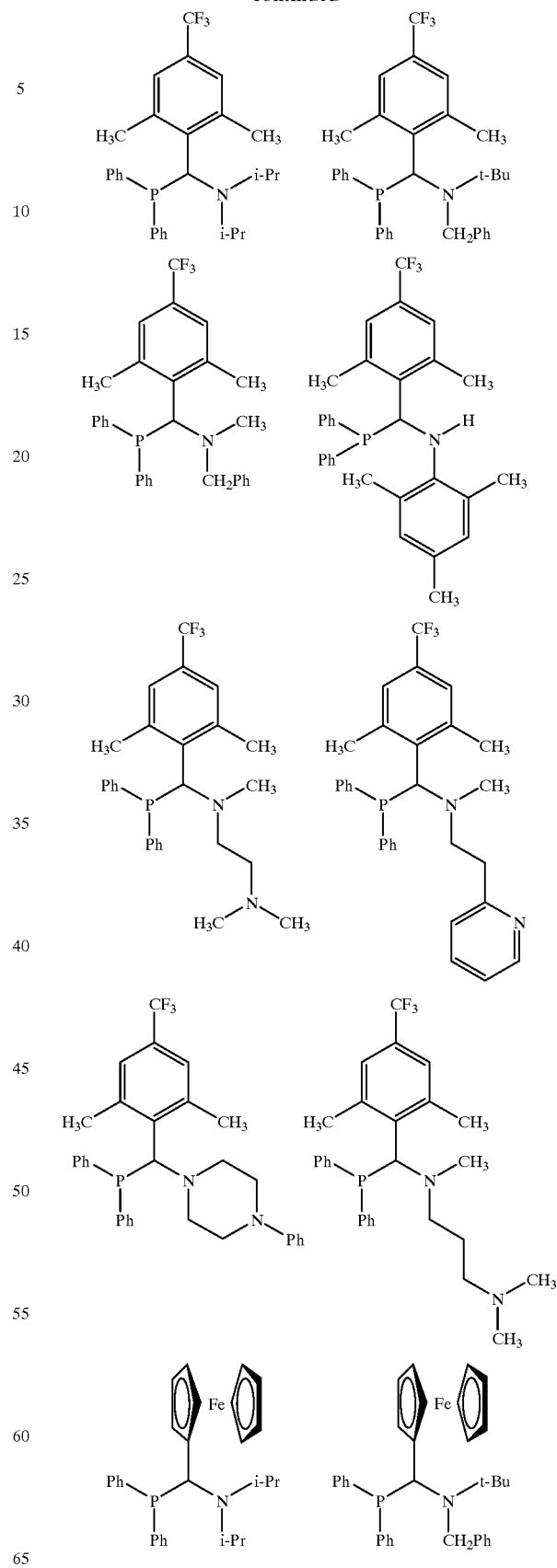

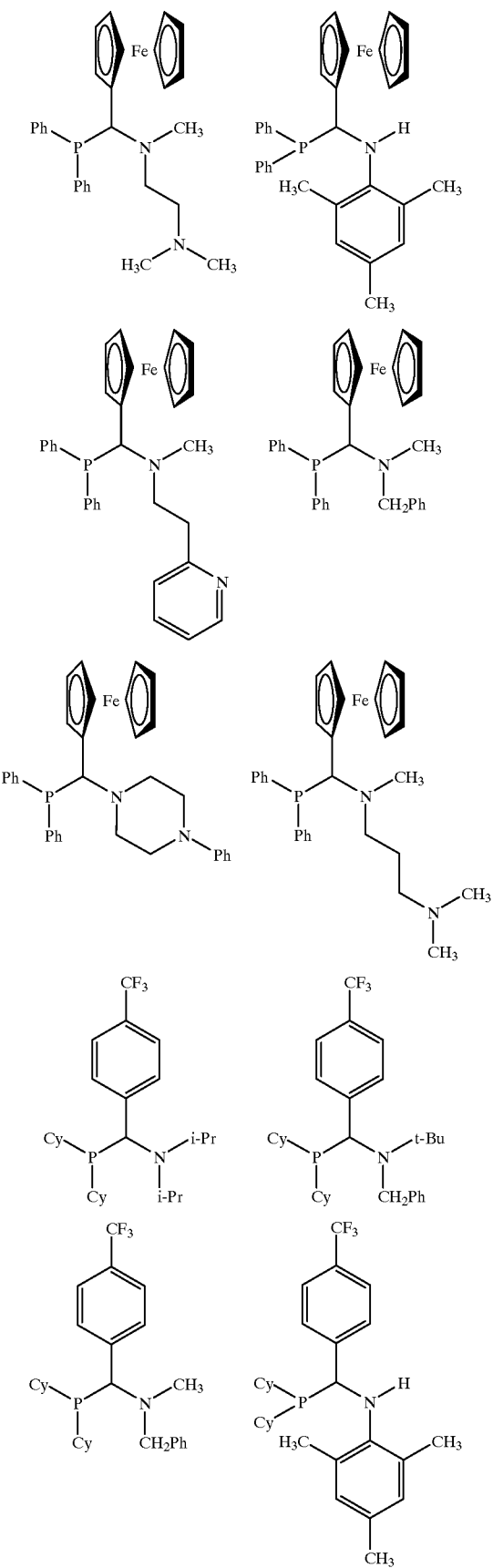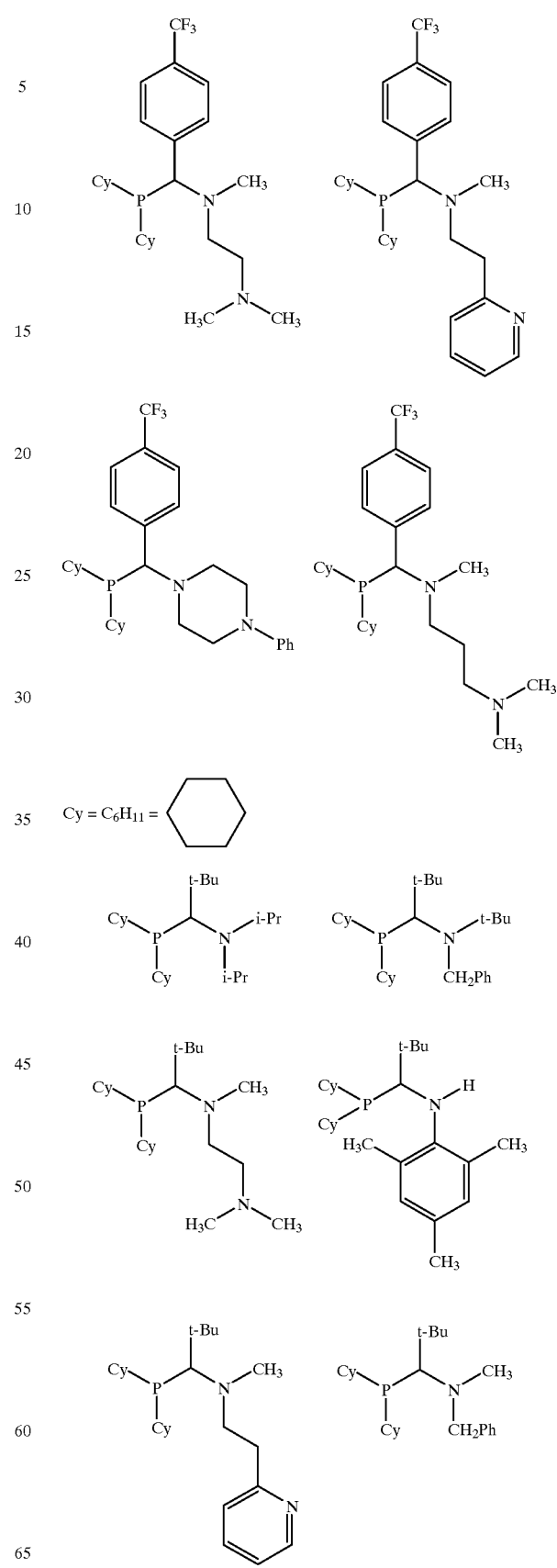

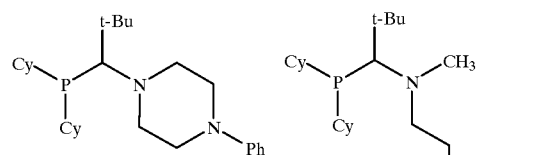
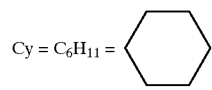
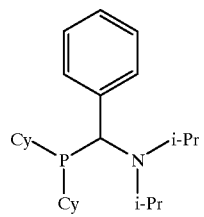
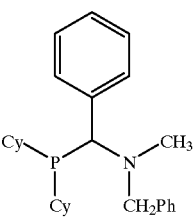
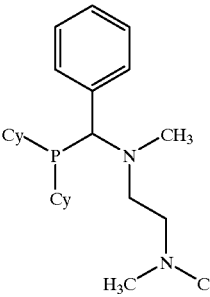
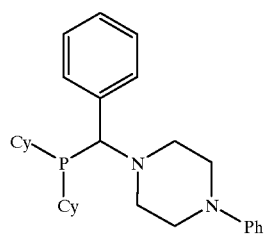
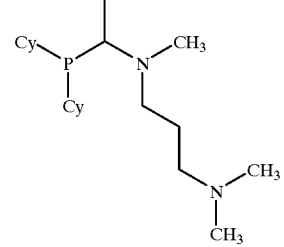
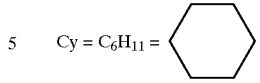
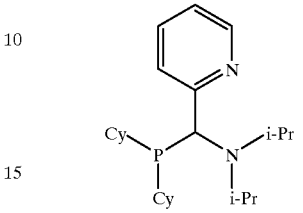
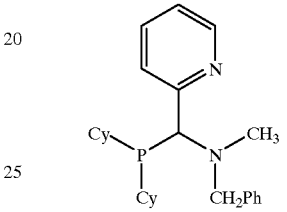
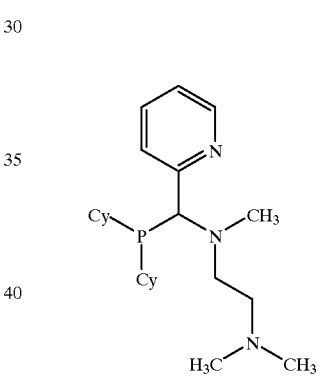
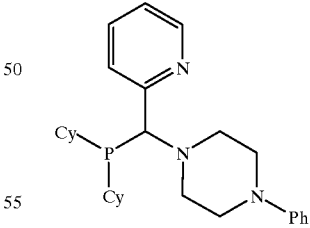
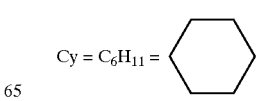

-continued

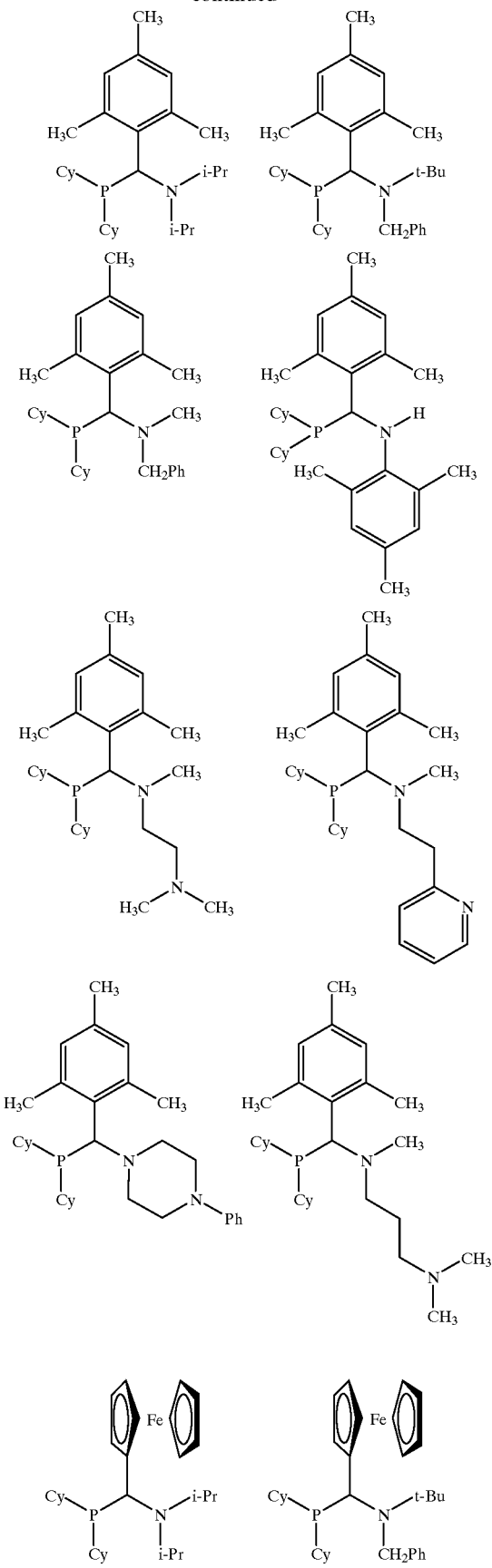

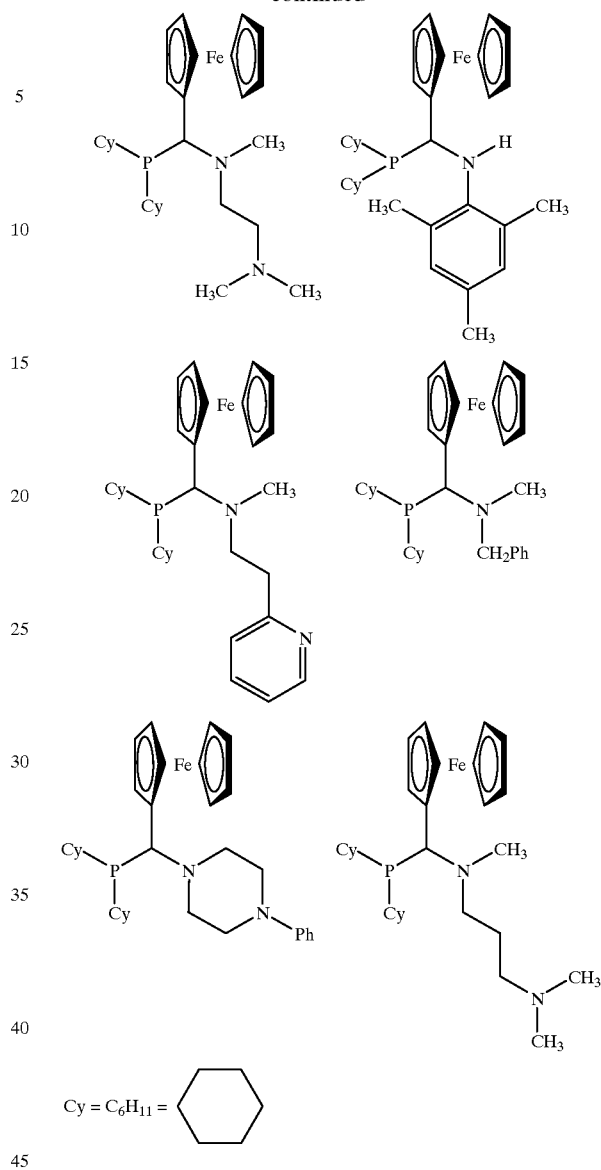

EXAMPLES 118–213:

Preparation of a 96-Member Coordination Complex Library: Using the 96 ligands that were formed in Examples 22–117, coordination complexes were formed with each member. In a glovebox, 500 μL of $Et_2O$ was added to each element of the 96 member ligand library. 100 μL of a 0.50 M solution of CODPdMeCl (COD≡1,5-cyclooctadiene) in $CH_2Cl_2$(0.05 mmol) was then added to each well and the mixture was shaken for 1 hour. Pentane (500 μL) was added to each well and the microtiter plate was shaken for 10 minutes to precipitate the product. Th e content s of eah well were then transferred by pipette to a filtering microtiter plate. The plate was filtered and each well was washed with pentane (1 mL). The contents of the microt iter plate were allowed to dry under a stream of $N_2$ and were stored in the glovebox. The color of the product ranged from dark red to colorless, and samples ranged from highly crystalline solids to powders to oily solids.

EXAMPLES 214–309:

Generation of a 96-member library of $\{(PCN)Pd(CH_3)(NCCH_3)\}^+$ $\{BAr'_4\}^-$. In a glovebox, $NaBAr'_4$ (40 mg/well; 0.05 mmol) was loaded into a microtiter plate using a solid-addition plate. This microtiter plate (plate #1) was placed into a filter block, and the microtiter plate containing the 96-member library (from examples 118–213, plate #2) was placed on top of the filter block. 500 µL of $CH_2Cl_2$ was added to each well of plate #2 to dissolve solid the (PCN)PdMeCl. A vaccum was then applied to the filter block to transfer the contents of plate #2 into plate #1. Acetonitrile (40 µL) was then added to each well of plate #1 and the plate was then sealed in a manner similar to that described for Examples 22–117. The microtiter plate was shaken for 2 hours. The seal was then removed and solvent was removed by blowing nitrogen over the plate for 5 hours. The plate was then dried in vacuo for 2 hours.

Example 310:

Polymerization of Ethylene: In a glovebox, {(PhCH$_2$)(CH$_3$)NCH(2-pyridine)P(C$_6$H$_5$)$_2$Pd(CH$_3$)(NCCH$_3$)}$^+$ {(BAr'$_4$)}$^-$ (17 mg, 0.011 mmol) was dissolved in 20 µL $CH_2Cl_2$ and the solution was loaded into a 50 µL Schlenk flask. The flask was removed from the glovebox and placed under 7 psi of ethylene. The reaction was stirred for 4 hours. Solvent was removed in vacuo, leaving a waxy solid (120 mg) whose $^1$H NMR spectrum matched that of polyethylene.

Example 311:

Pd/PCN-catalyzed aryl amination reaction: A mixture of 4-bromobiphenyl (264 mg, 1.13 mmol), morpholine(0.12 mL, 1.36 mmol, NaO-t-Bu (116 mg, 1.20 mmol), Pd(dba)$_2$ (12 mg, 20 µmol), ligand 1 (below) (18 mg, 45 µmol) in toluene (3 mL) was heated at 105° C. for 60 minutes. Analysis of an aliquot of the reaction mixture indicated 89% conversion of 4-bromobiphenyl starting material with the formation of the desired 4-morpholinobiphenyl product in 88% selectivity.

Ligand 1

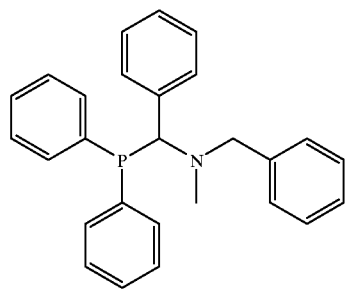

Example 312:

A Suzuki cross-coupling:

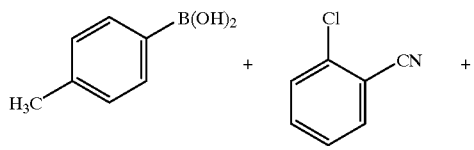

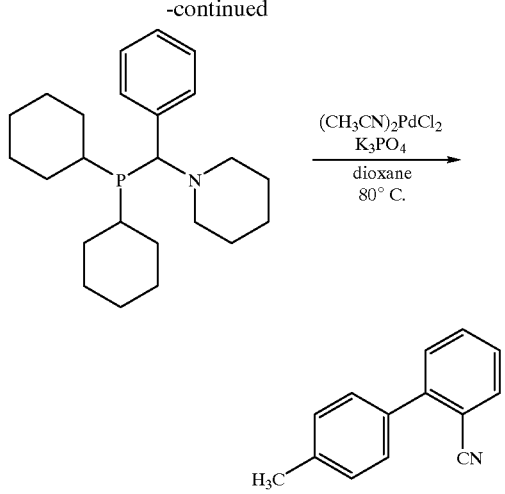

$K_3PO_4$ (1.70 g, 8.00 mmol), 2-chlorobenzonitrile (0.367 g, 2.67 mmol), and p-tolueneboronic acid (0.399 g, 2.93 mmol) were taken up in 11 ml of dry dioxane under nitrogen and a 1 ml aliquot from a solution containing ligand (10.0 mg, 53.4 µmol) and (CHCN$_3$)$_2$PdCl$_2$ (6.90 mg, 26.7 µmol) in 10 ml dry dioxane was added. The mixture was then heated to 80 ° C. for 12 hours. GC/MS of the solution showed that the reaction had proceeded to 21% completion.

Example 313:

A Ligand Library Synthesis, Complexation, Activation and Screening for Olefin Polymerization:

A: Synthesis of Library 1: An 8×12 array of pre-weighed 1.0 mL glass autosampler vials was assembled in an aluminum block. 1.0 M solutions of R$^3$R$^4$PH{Ph$_2$PH, Cy$_2$PH}, R'CHO{PhCHO, 4-CF$_3$C$_6$H4CHO, 2,4,6-(CH$_3$)$_3$C$_6$H$_2$CHO, 2-pyridylCHO, quinolinecarboxaldehyde, ferrocenylcarboxaldehyde}, and R$^1$R$^2$NH {(PhCH$_2$)(CH$_3$)NH, (n-C$_6$H$_{13}$)(CH$_3$)NH, (PhCH$_2$)(t-Bu)NH, (NCCH$_2$CH$_2$)(CH$_3$)NH, (Me$_2$NCH$_2$CH$_2$)NH(Me), (Me$_2$NCH$_2$CH$_2$CH$_2$)NHMe, N-phenylpiperazine, piperidine) in THF were prepared. 200 µL (0.2 mmol) of R$^1$R$^2$NH, R$^3$R$^4$PH, and R' CHO were dispensed into each viar using a liquid dispensing robot The plate was then covered with a sheet of Teflon and a sheet of butyl rubber. An aluminum plate was then clamped into place over the microtiter plate assembly, sealing off each member of the library. The microtiter plate was shaken overnight. The aluminum plate and butyl rubber and Teflon sheets were removed from the microtiter plate, and solvent was removed by blowing a stream of dry N$_2$ over each vial. The plate was then dried in vacuo. The PCN ligands are very air-sensitive and should be stored and handled under an inert atmosphere.

TABLE 1

Library Nomenclature for Example 313: $R^3R^4P = Ph_2P$

| Amine \ Aldehyde | PhCHO | 4-CF₃-C₆H₄CHO | mesityl-CHO | 2-pyridyl-CHO | 2-quinolyl-CHO | ferrocenyl-CHO |
|---|---|---|---|---|---|---|
| PhCH₂NHMe | A1 | A2 | A3 | A4 | A5 | A6 |
| n-hexyl-NHMe | B1 | B2 | B3 | B4 | B5 | B6 |
| PhCH₂NH-t-Bu | C1 | C2 | C3 | C4 | C5 | C6 |
| NC-CH₂CH₂-NHMe | D1 | D2 | D3 | D4 | D5 | D6 |
| Me₂N-(CH₂)₃-NHMe | E1 | E2 | E3 | E4 | E5 | E6 |
| Me₂N-(CH₂)₄-NHMe | F1 | F2 | F3 | F4 | F5 | F6 |
| N-phenylpiperazine | G1 | G2 | G3 | G4 | G5 | G6 |

TABLE 1-continued

33/54 Table 1 (Continued), but with $r^3r^4P = (C_6H_{11})_2P$

| | H1 | H2 | H3 | H4 | H5 | H6 |
|---|---|---|---|---|---|---|
| piperidine (NH) | A7 | A8 | A9 | A10 | A11 | A12 |
| benzyl-NH-Me | B7 | B8 | B9 | B10 | B11 | B12 |
| n-hexyl-NH-Me | C7 | C8 | C9 | C10 | C11 | C12 |
| benzyl-NH-t-Bu | D7 | D8 | D9 | D10 | D11 | D12 |
| NC-CH2CH2-NH-Me | E7 | E8 | E9 | E4 | E11 | E12 |
| Me2N-CH2CH2-NH-Me | | | | | | |

Aldehydes (columns H1–H6): benzaldehyde; 4-(trifluoromethyl)benzaldehyde; 2,4,6-trimethylbenzaldehyde; pyridine-2-carbaldehyde; quinoline-2-carbaldehyde; ferrocenecarbaldehyde.

TABLE 1-continued
| | F7 | F8 | F9 | F10 | F11 | F12 |
|---|---|---|---|---|---|---|
|  | G7 | G8 | G9 | G10 | G11 | G12 |
| 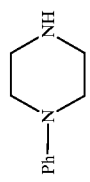 | H7 | H8 | H9 | H10 | H11 | H12 |
| 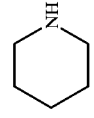 | | | | | | |

B: Library Characterization: 20 library elements were selected. The vials were weighed and the contents of each vial were dissolved in 0.70 μL of a 0.10 M solution of $(Me_3Si)_2O$ in $CDCl_3$. Yields were calculated by comparing the integration of a selected peak (usually $R_aR_bCHR_c$; d, δ=4–5.5 ppm)) to that of the internal standard. Purity (wt %) was calculated by dividing the yield (as calculated by NMR) by a conversion factor X (X=weight of product obtained/theoretical yield.) In some cases, the calculated purity exceeded 100% due to product loss by evaporation or routine losses during transfer; in these cases, purity was qualitatively analyzed by $^1H$ and $^{31}P$ NMR. Yields and purity data are shown in Table 2.

TABLE 2

Characterization of PCN Library: Yield, Purity and $^{31}P$ NMR Data for 20 Library Elements. (* = purity estimated by $^1H$ and $^{31}P$ NMR)

| Structure | Yield | Purity (wt. %) | $^{31}P$ NMR (δ) |
|---|---|---|---|
| [Cy₂P-CH(2-pyridyl)-N(Me)-CH₂CH₂CH₂-NMe₂] | 82% | 83% | −0.2 |
| [Ph₂P-CH(2-quinolyl)-N(Me)-CH₂CH₂-NMe₂] | 87% | 88% | −14.7 |
| [Ph₂P-CH(2-pyridyl)-N(piperidyl)] | 88% | 97% | −16.4 |
| [Cy₂P-CH(Fc)-N-piperazinyl-N-Ph], Fc = $(C_2H_5)Fe(C_5H_4)$ | 89% | 99% | 1.8 |
| [Ph₂P-CH(4-CF₃-C₆H₄)-N(Me)-n-C₆H₁₃] | 74% | 82% | −14.9 |
| [Ph₂P-CH(2-pyridyl)-N(Me)-CH₂CH₂CH₂-NMe₂] | 94% | 86%* | −18.0 |
| [Cy₂P-CH(4-CF₃-C₆H₄)-N-piperidyl] | 80% | >95%* | −6.4 |
| [Cy₂P-CH(4-CF₃-C₆H₄)-N(Me)-CH₂Ph] | 54% | 89%* | −4.1 |
| [Ph₂P-CH(Ph)-N-piperidyl] | 63% | 85% | −19.4 |

TABLE 2-continued
Characterization of PCN Library: Yield, Purity and ³¹P NMR Data for 20 Library Elements. (* = purity estimated by ¹H and ³¹P NMR)
| Structure | Yield | Purity (wt. %) | ³¹P NMR (δ) |
|---|---|---|---|
| 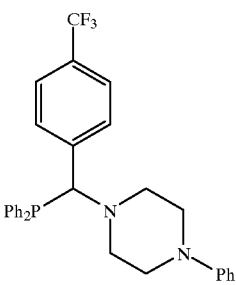 | 77% | 79% | −17.2 |
| 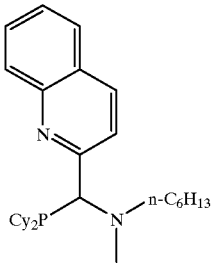 | 76% | 82% | −0.1 |
| 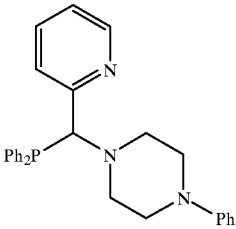 | 87% | 87% | −16.2 |
| 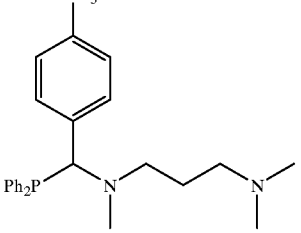 | 87% | 93% | −15.1 |
| 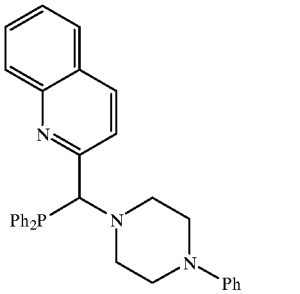 | 82% | 90% | −15.0 |
| 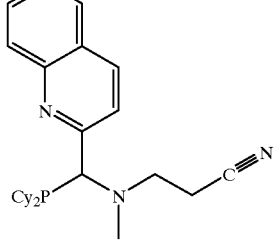 | 79% | 82% | 0.3 |
| 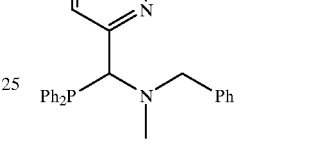 | 85% | 91% | −15.1 |
| 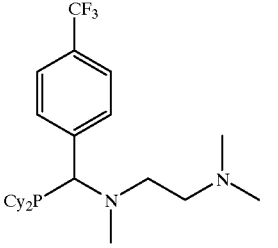 | 80% | 90% | −1.9 |
| 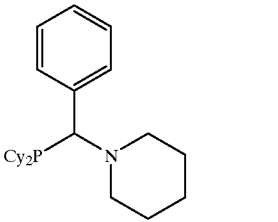 | 81% | >95%* | 4.5 |
| 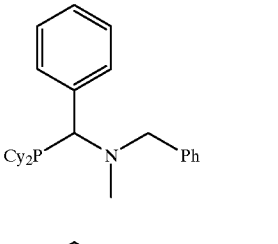 | 80% | 80%* | −1.8 |
| 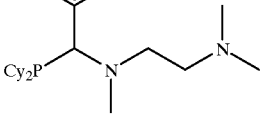 | 82% | 82% | −0.3 |

C: Screening of Library 1/(CODPdMeCl)/NaBAR'4 for Ethylene Polymerization: Ligands A4 and G7 were removed from the library, so these wells were run as "blanks". Using automated liquid dispensing techniques, 0.01 mmol of each library element was dispensed into a 15 mL pre-weighed glass tube. Solvent was removed from the tubes by evaporation, and 48 tubes were loaded into a Parallel Polymerization Reactor (PPR), described in detail in commonly assigned, U.S. patent applications Nos. 09/177,170, filed Oct. 22, 1998, 09/211,982, filed Dec. 14, 1998 and 09/239,223, filed Jan. 29, 1999 (having attorney docket no. 10555/003001), each of which is incorporated herein by reference. A 0.10 M solution of CODPdMeCl/0.5 M solution of $CH_3CN$ in $CH_2Cl_2$ was prepared, and 0.100 mL of this solution was dispensed into each tube, followed by 5.00 mL of $CH_2Cl_2$. After 1 hour, solid $NaBAr'^4$ (10 mg) was added and the PPR was pressurized with ethylene for 1.0 hour. At this point, the tubes were removed from the PPR and solvent was allowed to evaporate. The process was repeated for the remaining 48 tubes. The tubes were weighed, and the library elements that yielded more than 10 mg polymer are listed below in Table 3, although all the tubes showed yielded some production of polymer.

TABLE 3

Screen of $\{[PCN]Pd(CH_3)(NCCH_3)\}^+\{BAr'_4\}^-$/Ethylene in $CH_2Cl_2$ (Cutoff = 10 mg polymer = 36 turnovers/hour):

| Library element | Ligand structure | Yield polymer (mg.) | Activity (turnovers/hour) |
| --- | --- | --- | --- |
| C2 | [structure with CF3, Ph2P, N, Ph, t-Bu] | 33 | 118 |
| E2 | [structure with CF3, Ph2P, N, N] | 113 | 403 |
| G2 | [structure with CF3, Ph2P, N, N-Ph piperazine] | 62 | 221 |
| H2 | [structure with CF3, Ph2P, N piperidine] | 45 | 161 |
| E3 | [structure with mesityl, Ph2P, N, N] | 18 | 64 |
| B4 | [structure with pyridine, Ph2P, N, n-C6H13] | 103 | 368 |
| E4 | [structure with pyridine, Ph2P, N, N] | 15 | 54 |
| F4 | [structure with pyridine, Ph2P, N, N propyl linker] | 84 | 300 |
| H4 | [structure with pyridine, Ph2P, N piperidine] | 12 | 43 |

TABLE 3-continued

Screen of {[PCN]Pd(CH$_3$)(NCCH$_3$)}$^+${BAr'$_4$}$^-$/Ethylene in CH$_2$Cl$_2$ (Cutoff = 10 mg polymer = 36 turnovers/hour):

| Library element | Ligand structure | Yield polymer (mg.) | Activity (turnovers/hour) |
|---|---|---|---|
| B5 | (quinoline-CH(PPh$_2$)-N(CH$_3$)(n-C$_6$H$_{13}$)) | 35 | 125 |
| C5 | (quinoline-CH(PPh$_2$)-N(CH$_3$)(CH$_2$-t-Bu)Ph) | 20 | 72 |
| B5 | (quinoline-CH(PPh$_2$)-N(CH$_3$)CH$_2$CH$_2$N(CH$_3$)$_2$) | 62 | 221 |
| G5 | (quinoline-CH(PPh$_2$)-piperazine-N-Ph) | 52 | 186 |
| A6 | Ph$_2$P-CH(Fc)-N(CH$_3$)(CH$_2$Ph); Fc = (C$_5$H$_5$)Fe(C$_5$H$_4$) | 55 | 196 |
| C6 | Ph$_2$P-CH(Fc)-N(t-Bu)(CH$_2$Ph); Fc = (C$_5$H$_5$)Fe(C$_5$H$_4$) | 30 | 107 |
| D6 | Ph$_2$P-CH(Fc)-N(CH$_3$)(CH$_2$CH$_2$CN); Fc = (C$_5$H$_5$)Fe(C$_5$H$_4$) | 46 | 164 |
| H6 | Ph$_2$P-CH(Fc)-piperidine; Fc = (C$_5$H$_5$)Fe(C$_5$H$_4$) | 61 | 218 |

D: Screening of Library 1/Ni(CF$_3$CO$_2$)$_2$/300MAO for Ethylene Polymerization: 6.0×10$^{-4}$ mmol of library elements A1–6 were dispensed into glass tubes, followed by 200 μL of a 3×10$^{-3}$ M solution of Ni(TFA)$_2$ in Et$_2$O/ DCE (5% Et$_2$O by volume). The solvent was allowed to evaporate, and then the tubes were loaded into the PPR. 4.88 mL of toluene was added, followed by 120 μL of a 10% solution of MAO in toluene (300 equivalents). The PPR was then sealed up and pressurized with ethylene (50 psi) for 2.0 hours. The reactor was then vented and the tubes were removed. Solvent and low molecular weight oligomers were removed by evaporation. The process was repeated for library elements A7–H12. Polymers were obtained in all the polymerization experiments.

E: Screening of Library 1I/Cr(CF$_3$CO$_2$)3/300 MAO for Ethylene Polymerization: The library was set up as described above in part D. The PPR was then sealed up and pressurized with ethylene (50 psi) for 2.0 hours. The reactor was then vented and the tubes were removed. Solvent and low molecular weight oligomers were removed by evaporation. Polymers were obtained in all the polymerization experiments.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A process of polymerizing comprising contacting an addition polymerizable monomer with a catalyst, said catalyst comprising a compound characterized by one of the formulas:

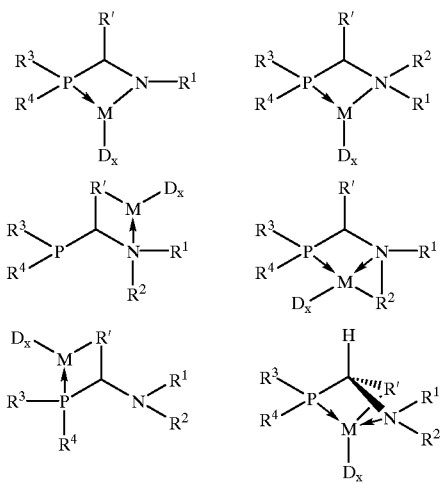

wherein each of R$^1$, R$^2$, R$^3$, and R$^4$ is, independently, selected from the group consisting of hydrogen, alkyl, substituted alkyl, saturated cyclic hydrocarbons, aryl, substituted aryl, arylalkyl, substituted arylalkyl, acyl, amino, alkylamino, acylamino, silyl, germyl, stanyl, siloxy, phosphino, aryloxy, aryloxyalkyl, substituted aryloxyalkyl, heteroaryl, substituted heteroaryl, heteroarylalkyl, substituted heteroarylalkyl, heterocycles, substituted heterocycles, heterocyclicalkyl, substituted heterocyclicalkyl S-aryl and S-alkyl mercaptans and combinations thereof; and optionally R$^1$ and R$^2$ are combined together to form a ring structure and optionally, R$^3$ and R$^4$ are combined together in a ring structure;

R' is selected from the group consisting of alkyl, substituted alkyl, aryl, substituted aryl, arylaLkyl, substituted arylalkyl, silyl, germyl, stanyl, phosphino, aryloxy, aryloxyalkyl, substituted aryloxyalkyl, heteroaryl, substituted heteroaryl, heteroarylalkyl, substituted heteroarylalkyl, heterocycles, substituted heterocycles, heterocyclicalkyl, substituted heterocyclicalkyl S-aryl and S-alkyl mercaptans and combinations thereof;

M is a metal selected from the group consisting of Groups 4–11 of the Periodic Table of Elements;

D is independently in each occurrence selected from the group consisting of alkyl, substituted alkyl, aryl, substituted aryl, arylalkyl, substituted arylalkyl, halogen, amino, silyl, germyl, oxo, sulfide, alkoxy, hydride, sulfonate, acteate and combinations thereof;

x is an integer from 1 to 3;

and an activator.

2. The process of claim 1 wherein R$^3$ and R$^4$ are independently selected from the group consisting of aryl, substituted aryl and saturated cyclic hydrocarbons.

3. The process of claim 1 wherein R$^3$ and R$^4$ are independently selected from the group consisting of phenyl, substituted phenyl and cyclohexyl.

4. The process of claim 1 wherein R' is selected from the group consisting of aryl and substituted aryl.

5. The process of claim 1 wherein R' is selected from the group consisting of 4-trifluoromethylphenyl, pyridyl, and quinolinyl.

6. The process of claim 1 wherein M is Ni, Pd, Ti, Mo, Fe, or Co.

7. The process of claim 1 wherein the monomer is selected from the group of ethylenically or acetylenically unsaturated monomers having from 2 to 20 carbon atoms or a combination thereof.

8. The process of claim 1 wherein the monomer comprises ethylene, propylene, 1-butene, 1-hexene, 1-octene, 4-methyl-pentene- 1, styrene or mixtures thereof.

9. The process of claim 1 wherein the monomer comprises an acetate or an acrylate.

10. The process of claim 1 wherein the activator comprises methylalumoxane, trimethylaluininum, AgBF$_4$ AgBPh$_4$ (where Ph=phenyl), NaBAr'$_4$ and/or H(OEt$_2$)$_2$BAr'$_4$ (where Et=ethyl).

11. The process of claim 1 wherein the catalyst is supported.

12. The process of claim 11 wherein the polymerization occurs in the gas or slurry phase.

13. The process of claim 1 wherein the polymerization occurs in suspension or solution.

14. The process of claim 1 further comprising a scavenger.

* * * * *

UNITED STATES PATENT AND TRADEMARK OFFICE
CERTIFICATE OF CORRECTION

PATENT NO. : 6,177,528 B1
DATED : January 23, 2001
INVENTOR(S) : LaPointe et al.

It is certified that error appears in the above-identified patent and that said Letters Patent is hereby corrected as shown below:

Column 47,
Line 36, replace the word "arylaLkyl" with -- arylalkyl --

Column 48,
Line 33, delete the word "trimethylaluininum" with -- trimethylaluminum --

Signed and Sealed this

Eighteenth Day of February, 2003

JAMES E. ROGAN
*Director of the United States Patent and Trademark Office*